US010835449B2

(12) United States Patent
Lewis et al.

(10) Patent No.: US 10,835,449 B2
(45) Date of Patent: Nov. 17, 2020

(54) MODULAR COMPONENTS FOR MEDICAL DEVICES

(71) Applicant: ZOLL MEDICAL CORPORATION, Chelmsford, MA (US)

(72) Inventors: James Lewis, Needham, MA (US); Guy R. Johnson, Gloucester, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 914 days.

(21) Appl. No.: 15/084,116

(22) Filed: Mar. 29, 2016

(65) Prior Publication Data
US 2016/0287470 A1 Oct. 6, 2016

Related U.S. Application Data

(60) Provisional application No. 62/139,997, filed on Mar. 30, 2015.

(51) Int. Cl.
*A61B 5/00* (2006.01)
*A61H 31/00* (2006.01)
(Continued)

(52) U.S. Cl.
CPC .......... *A61H 31/005* (2013.01); *A61B 5/046* (2013.01); *A61B 5/04085* (2013.01);
(Continued)

(58) Field of Classification Search
CPC .................................................. A61H 31/005
See application file for complete search history.

(56) References Cited

U.S. PATENT DOCUMENTS 3,862,636 A   1/1975  Bell et al.
3,886,950 A   6/1975  Ukkestad et al.
(Continued)

FOREIGN PATENT DOCUMENTS

EP     0707825 A2    4/1996
EP     0761255 A1    3/1997
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.
(Continued)

*Primary Examiner* — Jennifer Pitrak McDonald
*Assistant Examiner* — Jennifer L Ghand
(74) *Attorney, Agent, or Firm* — Finch & Maloney PLLC

(57) ABSTRACT

A medical device is disclosed that includes a service component for use in detecting patient data, at least one processor coupled with the service component, a care protocol module executable by the at least one processor to provide healthcare to a patient at least in part by generating a request for processing by the service component, and a resource module executable by the at least one processor to manage access to the service component by identifying a level of service associated with the care protocol module and responding to the request by managing the service component to meet the level of service. The care protocol module implements a patient care protocol that includes a sequence of actions directed to the patient. The level of service indicates a level of performance that the patient care protocol requires of the resource module. Selective offloading of modular functions is also enabled.

19 Claims, 15 Drawing Sheets

(51) Int. Cl.
*A61N 1/39* (2006.01)
*G16H 40/63* (2018.01)
*A61B 5/046* (2006.01)
*A61B 5/0408* (2006.01)
*A61B 5/11* (2006.01)

(52) U.S. Cl.
CPC ......... *A61B 5/6805* (2013.01); *A61H 31/006* (2013.01); *A61N 1/3925* (2013.01); *A61N 1/3987* (2013.01); *G16H 40/63* (2018.01); *A61B 5/11* (2013.01); *A61H 2201/1207* (2013.01); *A61H 2201/1619* (2013.01); *A61H 2201/1652* (2013.01); *A61H 2201/5007* (2013.01); *A61H 2201/5043* (2013.01); *A61H 2201/5046* (2013.01); *A61H 2201/5048* (2013.01); *A61H 2201/5082* (2013.01); *A61H 2201/5084* (2013.01); *A61H 2201/5092* (2013.01); *A61H 2201/5097* (2013.01); *A61H 2230/04* (2013.01); *A61H 2230/06* (2013.01); *A61H 2230/207* (2013.01); *A61H 2230/30* (2013.01); *A61H 2230/65* (2013.01)

(56) References Cited

U.S. PATENT DOCUMENTS

| | | | |
|---|---|---|---|
| 4,088,138 A | 5/1978 | Diack et al. |
| 4,576,170 A | 3/1986 | Bradley et al. |
| 4,580,572 A | 4/1986 | Granek et al. |
| 4,583,547 A | 4/1986 | Granek et al. |
| 4,619,265 A | 10/1986 | Morgan et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,097,830 A | 3/1992 | Eiketjord et al. |
| 5,381,798 A | 1/1995 | Burrows |
| 5,607,454 A | 3/1997 | Cameron et al. |
| 5,645,571 A | 7/1997 | Olson et al. |
| 5,741,306 A | 4/1998 | Glegyak et al. |
| 5,792,190 A | 8/1998 | Olson et al. |
| 5,919,212 A | 7/1999 | Olson et al. |
| 5,929,601 A | 7/1999 | Kaib et al. |
| 5,944,669 A | 8/1999 | Kaib |
| 6,006,132 A | 12/1999 | Tacker, Jr. et al. |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,304,783 B1 | 10/2001 | Lyster et al. |
| 6,336,900 B1 | 1/2002 | Alleckson et al. |
| 6,374,138 B1 | 4/2002 | Owen et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,681,003 B2 | 1/2004 | Linder et al. |
| 6,690,969 B2 | 2/2004 | Bystrom et al. |
| 6,694,191 B2 | 2/2004 | Starkweather et al. |
| 6,751,501 B1 | 6/2004 | Schuler et al. |
| 6,804,554 B2 | 10/2004 | Ujhelyi et al. |
| 6,889,078 B2 | 5/2005 | Struble et al. |
| 6,889,079 B2 | 5/2005 | Bocek et al. |
| 6,908,437 B2 | 6/2005 | Bardy |
| 6,961,612 B2 | 11/2005 | Elghazzawi et al. |
| 6,990,373 B2 | 1/2006 | Jayne et al. |
| 7,088,233 B2 | 8/2006 | Menard |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,627,372 B2 | 12/2009 | Vaisnys et al. |
| 7,712,373 B2 | 5/2010 | Nagle et al. |
| 7,831,303 B2 | 11/2010 | Rueter et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,005,552 B2 | 8/2011 | Covey et al. |
| 8,121,683 B2 | 2/2012 | Bucher et al. |
| 8,140,154 B2 | 3/2012 | Donnelly et al. |
| 8,224,441 B2 | 7/2012 | Vaisnys et al. |
| 8,271,082 B2 | 9/2012 | Donnelly et al. |
| 8,319,632 B1 | 11/2012 | Vaisnys et al. |
| 8,331,574 B2 | 12/2012 | Powers |
| 8,364,221 B2 | 1/2013 | Mannheimer et al. |
| 8,369,944 B2 | 2/2013 | Macho et al. |
| 8,406,842 B2 | 3/2013 | Kaib et al. |
| 8,494,628 B2 | 7/2013 | Vaisnys et al. |
| 8,548,584 B2 | 10/2013 | Jorgenson |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,781,577 B2 | 7/2014 | Freeman |
| 8,880,196 B2 | 11/2014 | Kaid |
| 8,897,860 B2 | 11/2014 | Volpe et al. |
| 8,904,214 B2 | 12/2014 | Volpe et al. |
| 9,283,399 B2 | 3/2016 | Donnelly et al. |
| 2001/0031991 A1 | 10/2001 | Russial |
| 2002/0143278 A1* | 10/2002 | Bystrom .............. A61H 31/005 601/41 |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0195567 A1 | 10/2003 | Jayne et al. |
| 2003/0212311 A1 | 11/2003 | Nova et al. |
| 2004/0049233 A1 | 3/2004 | Edwards |
| 2004/0143297 A1 | 7/2004 | Ramsey |
| 2004/0214148 A1* | 10/2004 | Salvino ................ A61N 1/39 434/262 |
| 2004/0249419 A1 | 12/2004 | Chapman et al. |
| 2005/0027173 A1* | 2/2005 | Briscoe ............... G06F 19/325 600/300 |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0025696 A1* | 2/2006 | Kurzweil ........... A61B 5/04525 600/509 |
| 2006/0136000 A1 | 6/2006 | Bowers |
| 2006/0155336 A1* | 7/2006 | Heath .................. G16H 10/65 607/5 |
| 2006/0211934 A1 | 9/2006 | Hassonjee et al. |
| 2006/0259080 A1 | 11/2006 | Vaisnys et al. |
| 2006/0270952 A1 | 11/2006 | Freeman et al. |
| 2007/0073120 A1 | 3/2007 | Li et al. |
| 2007/0162075 A1 | 7/2007 | O'Hara |
| 2007/0239214 A1 | 10/2007 | Cinbis |
| 2008/0033495 A1 | 2/2008 | Kumar |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0177341 A1 | 7/2008 | Bowers |
| 2008/0249591 A1 | 10/2008 | Gaw et al. |
| 2008/0266118 A1 | 10/2008 | Pierson et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |

(56) References Cited

U.S. PATENT DOCUMENTS

| | | |
|---|---|---|
| 2009/0146822 A1 | 6/2009 | Soliman |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0010559 A1 | 1/2010 | Zhang et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0241181 A1 | 9/2010 | Savage et al. |
| 2010/0298899 A1 | 11/2010 | Donnelly et al. |
| 2010/0305462 A1 | 12/2010 | Callas et al. |
| 2010/0312297 A1 | 12/2010 | Volpe et al. |
| 2011/0022105 A9 | 1/2011 | Owen et al. |
| 2011/0080294 A1 | 4/2011 | Tanishima et al. |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0259377 A1 | 10/2012 | Freeman |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0004814 A1 | 1/2014 | Elghazzawi |
| 2014/0031884 A1 | 1/2014 | Elghazzawi et al. |
| 2014/0031885 A1 | 1/2014 | Elghazzawi et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0288609 A1 | 9/2014 | Freeman |
| 2014/0288610 A1 | 9/2014 | Freeman |
| 2014/0303680 A1 | 10/2014 | Donnelly et al. |
| 2014/0324112 A1 | 10/2014 | Macho et al. |
| 2015/0035654 A1 | 2/2015 | Kaib et al. |
| 2015/0039039 A1 | 2/2015 | Macho et al. |
| 2015/0039042 A1 | 2/2015 | Amsler et al. |
| 2015/0039053 A1 | 2/2015 | Kaib et al. |
| 2015/0080699 A1 | 2/2015 | Kaib et al. |
| 2015/0224330 A1 | 8/2015 | Kaib et al. |

FOREIGN PATENT DOCUMENTS

| | | |
|---|---|---|
| EP | 1642616 A2 | 4/2006 |
| JP | 2002509472 A | 3/2002 |
| JP | 2002-514107 A | 5/2002 |
| JP | 2006136707 A | 6/2006 |
| JP | 2007522859 A | 8/2007 |
| JP | 2008-302228 A | 12/2008 |
| JP | 2008302225 A | 12/2008 |
| JP | 2009510631 A | 3/2009 |
| JP | 2009-521865 A | 6/2009 |
| JP | 2009536068 A | 10/2009 |
| WO | 83/04171 A1 | 12/1983 |
| WO | 1997022297 A1 | 6/1997 |
| WO | 1998039061 A2 | 9/1998 |
| WO | 2000030529 A1 | 6/2000 |
| WO | 2004054656 A1 | 7/2004 |
| WO | 2004067083 A2 | 8/2004 |
| WO | 2004078259 A1 | 9/2004 |
| WO | 2007019325 A2 | 2/2007 |
| WO | 2009034506 A1 | 3/2009 |
| WO | 2009122277 A2 | 10/2009 |
| WO | 2012006524 A1 | 1/2012 |
| WO | 2012100219 A1 | 7/2012 |
| WO | 2013040214 A1 | 3/2013 |
| WO | 2013130957 A2 | 9/2013 |
| WO | 2014018160 A1 | 1/2014 |
| WO | 2014097035 A1 | 6/2014 |

OTHER PUBLICATIONS

Herlihy et al., "The Art of Multiple Processor Programming", Chapter 1, p. 1, Mar. 3, 2008.

http://web.archive.org/web/20030427001846/http:/www.lifecor.comiimagelib/imageproduct.asp. Published by LifeCor, Inc., 2002, on a webpage owned by LifeCor, Inc.

Wikipedia, "Automated External Defibrillator", May 31, 2009, Wikipedia, Section on Mechanism of Operation.

Wikipedia, "Multi-Core Processor", Dec. 11, 2009, <http://web.archive.org/web/20091211134408/http://en.wikipedia.org/wiki/Multicore_processor#Hardware>.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

* cited by examiner

FIG. 13A

| Current State | Requested State | Action Function |
|---|---|---|
| Idle | Charge | Charge() |
| Idle | Dump | DumpCharge() |
| Idle | SilentCharge | SilentCharge() |
| SilentCharge | Charge | Charge() |
| Charge | Charge | Charge() |
| Charge | Dump | DumpCharge () |
| Ready | Armed | Arm() |
| Ready | Dump | Dump() |
| Ready | Idle | Idle() |
| Armed | Shock | Shock() |
| Armed | Dump | Dump() |
| Armed | Idle | Idle() |
| Armed | SilentShock | SilentShock() |

Table 2: Transition Table showing Defibrillator Engine Resource Transisitions

FIG. 13B

| Requestor | Requestor ID | Requestor Priority |
|---|---|---|
| Audible Charge Request | ACR1 | 1 |
| Silent Charge Request | SCR2 | 2 |

Table 3: Table showing requestor priority

United States Patent US 10,835,449 B2

MODULAR COMPONENTS FOR MEDICAL DEVICES

RELATED APPLICATION

This application claims the benefit of U.S. Provisional Application No. 62/139,997 filed on Mar. 30, 2015, which is herein incorporated by reference in its entirety.

FIELD OF THE DISCLOSURE

This disclosure relates to medical devices, and more particularly, to arrangements of components within medical devices.

BACKGROUND

Contemporary medical devices are capable of supporting multiple treatment scenarios. For example, some medical devices monitor information representative of a patient's physiological condition and record this information for future reference. Other medical devices actively intervene and deliver therapy to patients. Some of these therapeutic medical devices use a patient's physiological information to determine whether delivery of therapy to a patient is appropriate.

An example of one such therapeutic medical device is an automated external defibrillator (AED). An AED is a medical device that is capable of automatically diagnosing when a patient fitted with the device is experiencing a cardiac arrhythmia (specifically, for example, ventricular fibrillation or ventricular tachycardia), and treating that patient by application of electrical shock therapy configured to stop (defibrillate) the arrhythmia, so that the heart can return to a normal rhythm. AEDs are designed to be simple to use and may include audio and/or visual commands, thereby allowing competent use by a layperson. However, the underlying functionality and requisite control that allows for such simplified use involves a number of non-trivial issues.

BRIEF DESCRIPTION OF THE DRAWINGS

FIG. 13A illustrates an example of a populated conflict resolution table that may be referenced during operations and interactions, according to an embodiment of the present disclosure.

FIG. 13B illustrates an example of a populated source component priority table that may be referenced during operations and interactions, according to an embodiment of the present disclosure.

The accompanying drawings are not intended to be drawn to scale. In the drawings, components that are identical or nearly identical may be represented by a like numeral. For purposes of clarity, not every component is labeled in every drawing.

DETAILED DESCRIPTION

Figure 1:
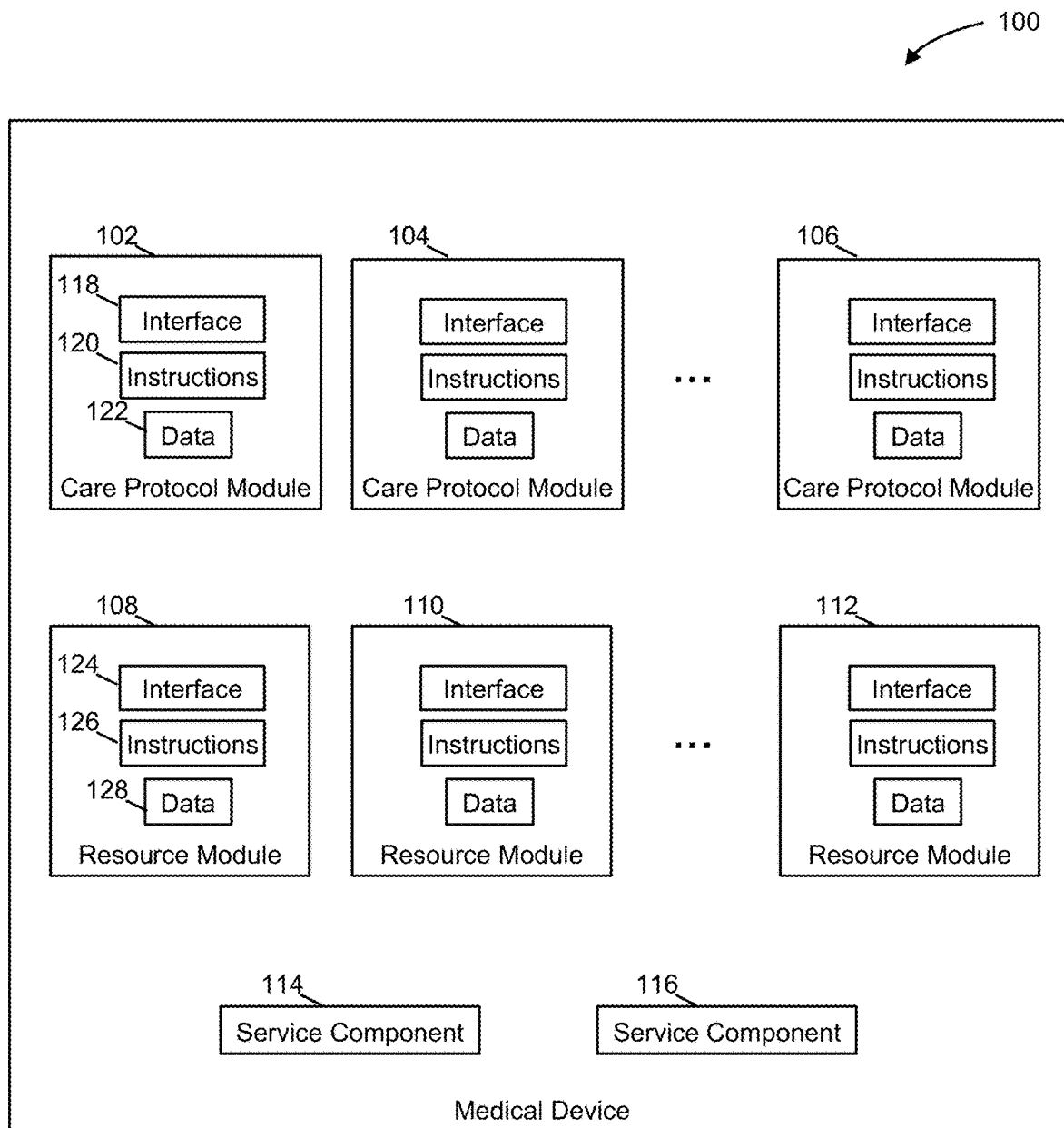
FIG. 1 illustrates an example medical device configured to execute multiple treatment protocols, in accordance with an embodiment of the present disclosure.

Medical devices in accordance with at least some embodiments disclosed herein implement a software architecture that includes care protocol modules and resource modules. Each of the modules can be implemented in a discrete fashion, so as to provide a degree of modularity to the architecture. The care protocol modules are programmed to control one or more operations of a given medical device, and the resource modules are programmed to interface with common service components (e.g., hardware and/or other software features) accessible to that medical device and which may be called upon or otherwise used in executing a care protocol. Thus, the resource modules effectively provide access to common service components that support care protocol modules. Working together within the software architecture, the care protocol modules and resource modules are cohesive units that implement medical device functionality in a loosely coupled system. This loose coupling enables a given medical device to discretely execute individual care protocol modules, thereby easing development and testing of medical device functionality. In some embodiments, the architecture may be executed in either a stand-alone mode or a distributed mode. In the stand-alone mode, the various resource and/or care protocol modules of the medical device are executed within the medical device itself, in response to the default configuration of the medical device or in response to no companion system being detected, in some example cases. In the distributed mode, some of the resource and/or care protocol modules of the medical device are executed on a companion system, in response to that companion system being detected and verified by the medical device. Numerous variations and embodiments will be appreciated in light of this disclosure.

General Overview

As previously explained, the underlying functionality and requisite control that allows for simplified use of a given piece of medical equipment, such as an AED, involves a number of non-trivial issues. For example, an AED uses a patient's physiological information to determine whether delivery of electrical shock therapy to a patient is appropriate. This ability of an AED to adapt to a given patient's situation can eliminate or otherwise mitigate a life threatening cardiac episode. Unfortunately, along with such adaptability comes increased device complexity and testing requirements. Increased complexity and testing requirements, in turn, increase the cost of initial medical device development as well as any subsequently developed medical device enhancements. In addition, where subsequently developed medical device enhancements overlap with existing medical device functionality, medical devices may need to be recertified by government regulators or other applicable authorities to ensure the medical devices are safe for prescriptive use.

Thus, techniques are provided herein for modularizing medical devices. It is believed that such modularization will ease development and testing of medical device functionality, and therefore allow for more rapid deployment of newly developed medical device technology for use by patients and their healthcare providers. In accordance with some embodiments, the techniques are implemented in medical devices having a software architecture that includes care protocol modules and resource modules. Each of the modules can be implemented in a discrete fashion, so as to provide modularity to the architecture. As will be appreciated, such modularity allows for code or other logic based changes and updates to be implemented in a compartmentalized fashion. Thus, rather than having to recertify the entire system of the medical device, recertification can be, for example, limited to the modules that actually changed and the modules that interact with those modules. The care protocol modules are programmed to control one or more operations of a given medical device, and the resource modules are programmed to interface with common service components (e.g., hardware and/or other software features) accessible to that medical device and which may be called upon or otherwise used in executing a care protocol. Thus, the resource modules provide stable and predictable access to common service components that support care protocol modules. Working together within the software architecture, the care protocol modules and resource modules are cohesive units that implement medical device functionality in a loosely coupled system. This loose coupling enables a given medical device to discretely execute individual care protocol modules, thereby easing development and testing of medical device functionality, as will be further appreciated in light of this disclosure.

In some embodiments, care protocol modules implement patient care protocols that include a sequence of actions that can be repeated, terminated, or altered dynamically. Examples of patient care protocols include heart monitoring protocols, CPR protocols, ventilation protocols, intubation protocols, defibrillation protocols, and the like. Resource modules, on the other hand, can be used, for example, to manage common hardware and software service components that may be required by a given care protocol module to support care protocol execution by the medical device. Examples of service components that can be managed by resource modules include user interface components (e.g., display and microphone), therapy delivery components (e.g., defibrillation capacitor and charging circuitry), sensor components (e.g., patient impedance data collectors to ensure electrodes are making proper contact with patient, accelerometers to monitor depth of chest compressions for CPR-based feedback, pulse detection sensor, oxygen level sensor, and ECG signal monitors), network interface components (e.g., Wi-Fi discovery and handshake protocols), or other medical device components that can be used to support a patient care protocol.

In some embodiments, the various resource and/or care protocol modules may be distributed, such that some modules are within the medical device itself, and other modules are offloaded or otherwise external to the medical device. For instance, in some example cases, some of the resource and/or care protocol modules are offloaded to a mobile computing system that is communicatively coupled with the medical device via a local network, wherein the mobile computing system includes suitable resources as well as an application programmed to interact with the medical device over the local network. The mobile computing system may be, for example, a smartphone or tablet or other suitable companion computing system (e.g., desktop, laptop, etc). The network may be wired, wireless, or a combination thereof, using any suitable communication network technology (e.g., Wi-Fi, Bluetooth, Ethernet, Internet, to name a few). This offloading of modular functions to a companion system can be done selectively, in that the medical device may either operate in a first mode where all modules are executed within the medical device when no network or verifiable companion device is detected (i.e., stand-alone mode), and in a second mode where one or more modules are offloaded from the medical device to the companion system when a network connection is detected and the companion system is authenticated (i.e., distributed mode).

In one specific example embodiment, the medical device is an AED and the companion device is a tablet computer having an application loaded thereon that is configured to interact with the AED via a local wireless network (LAN). In response to the AED detecting the presence of the tablet via a LAN-based discovery/handshake protocol and verifying the authenticity of the tablet application, the AED is further programmed or otherwise configured to assign some of its modular functions (e.g., display module, ECG rhythm analysis module, compression analysis module, CPR timing module, user prompting module, to name a few) to the tablet based application. In such a case, while the AED may also have a display, the tablet display may be better (e.g., larger, with color). Thus, offloading the display module may be beneficial. Note that having the tablet handle less critical or otherwise benign modular functions may be easier to recertify than other more critical modular functions. However, that is not to say that such critical modular functions cannot be offloaded. For instance, in still other embodiments, the AED may offload to the tablet at least some of the rescue functions, such as a rhythm analysis module.

In another embodiment, note that the companion device need not be local to the medical device. For instance, in one such case, the medical device is an AED that is capable of offloading at least some functions to a remote companion device such as a server system that is part of a cloud-based healthcare provider service. In such cases, the network communicatively coupling the AED to the remote companion device may be, for example, a local wireless network that is operatively coupled to the Internet. The AED at the rescue site can therefore access the cloud-based service and stream, for example, real-time video, ECG, CPR acceleration, patient impedance, and cable data to the cloud-based service, and the cloud-based service can stream back to the rescue site appropriate audio commands to assist in the treatment of the patient.

Thus, the AED may be fully capable of operating in a stand-alone mode and inexpensive to build, yet the AED may be even more effective by virtue of the features offered by a local or remote companion computer/application (e.g., better display, better processor, better communication, expert guidance, easier upgrade, to name a few features that might be improved by the use of a companion computing system or cloud-based service). In still further embodiments, professional healthcare provider features can be offered to the tablet application (e.g., manual charge/shock capability). In a more general sense, the AED can be modified to let any of its modular functions (e.g., rescue protocol and rhythm analysis functions) be handled remotely.

Medical Device Software Architecture

FIG. 1 illustrates a software architecture that uses care protocol modules and resource modules to implement multiple patient care protocols within the context of a medical device 100, according to an embodiment of the present disclosure. As shown in FIG. 1, the medical device 100 executes care protocol modules 102, 104, and 106 and resource modules 108, 110, and 112. The medical device 100 may be any of a variety of medical devices including defibrillators, monitors, CPR systems, and other medical devices. Examples of the medical device are described further below with reference to FIGS. 3-5.

Continuing with FIG. 1, the care protocol module 102 includes an interface 118, instructions 120, and data 122. Each of the care protocol modules 104 and 106 include an interface, instructions, and data analogous to the interface 118, instructions 120, and data 122 of the care protocol module 102. These analogous elements are structured and operate within their respective care protocol modules as the interface 118, instructions 120, and data 122 are structured and operate within the care protocol module 102. The resource module 108 includes an interface 124, instructions 126, and data 128. Each of the resource modules 110 and 112 include an interface, instructions, and data analogous to the interface 124, instructions 126, and data 128 of the resource module 108. These analogous elements are structured and operate within their respective resource modules as the interface 124, instructions 126, and data 128 are structured and operate within the resource module 108. The medical device 100 further includes common service components 114 and 116.

According to various embodiments, the service components 114 and 116 may include any hardware or software component utilized by a plurality of care protocol modules or resource modules. Examples of service components 114 and 116 include user interface hardware and software, network interface hardware and software, processing components (e.g., a general purpose process, digital signal processor, virtual machine, application-specific integrated circuits, field programmable gate arrays), power components, sensor components, therapy delivery components, and data storage components. Other examples of service components include, for instance, defibrillator subsystems (which may be charged prior to delivery of a therapeutic shock), non-invasive blood pressure (NIBP) controls, data recording devices, and control input detectors.

Although FIG. 1 depicts three care protocol modules, three resource modules, and two service components, the embodiments disclosed herein are not limited to a particular number or configuration of care protocol modules, resource modules, or service components. It will be further appreciated in light of this disclosure that multiple care protocol modules and resource modules may execute concurrently and exchange (i.e., transmit and/or receive) information to implement design behavior of the medical device. Further note that, due to the discrete and loosely coupled nature of the care protocol and resource modules, upgrades to individual care protocol and resource modules may be performed without impacting other components of the medical device 100.

It will be further appreciated in light of this disclosure that the care protocol modules and the resource modules may be implemented using hardware elements, software elements, or a combination of both. Examples of hardware elements may include processors, microprocessors, circuits, circuit elements (for example, transistors, resistors, capacitors, inductors, and sub-circuits made therefrom), integrated circuits, application-specific integrated circuit (ASICs), programmable logic devices (PLDs), digital signal processors (DSPs), field-programmable gate arrays (FPGAs), logic gates and gate-level circuitry, registers, semiconductor devices, chip or chip-set, microchips, and physical circuitry. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. In some embodiments, such software is implemented in conjunction with one or more electronic processing environments capable of executing that software. On the other hand, a pure software embodiment includes, for example, one or more non-transitory machine readable mediums encoded with instructions that when executed by one or more processor cause a methodology as variously provided herein to be carried out. The machine readable medium(s) can be any non-transitory memory, such as ROM, RAM, server, disc, thumb drive, register or set of registers, hard drive, on-chip memory, processor cache, or any other physical memory facilities. Numerous computer program products will be appreciated in light of this disclosure. Determining whether an embodiment is implemented using hardware elements and/or software elements may vary in accordance with any number of factors, such as desired processing cycle budget, computational rate, input data rates, output data rates, memory resources, data bus speeds, power level, heat tolerances, and other design or performance constraints.

In some embodiments, one or more of the various modules used to implement the functionality of a given medical device, such as the care protocol modules and the resource modules, may be referred to herein as "circuits" or "circuitry" rather than module (e.g., a care protocol circuit and a resource circuit). The terms "circuit" or "circuitry," as used in any embodiment herein, refer to a functional arrangement of hardware (e.g., gate-level logic or purpose built semiconductor) or a functional combination of hardware and software (e.g., electronic processor plus executable instructions). For example, the terms "circuit" or "circuitry" may comprise, for example, singly or in any combination, hardwired circuitry, programmable circuitry such as computer processors comprising one or more individual instruction processing cores, state machine circuitry, and/or firmware that stores instructions executed by programmable circuitry. The circuitry may include a processor and/or controller configured to execute one or more instructions to perform one or more operations described herein. The instructions may be embodied as, for example, an application, software, firmware, etc. configured to cause the circuitry to perform any of the various functionalities as provided herein. Software may be embodied as a software package, code, instructions, instruction sets and/or data recorded on a computer-readable storage device. Software may be embodied or implemented to include any number of processes, and processes, in turn, may be embodied or implemented to include any number of threads, etc., in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit, an ASIC, a system on-chip (SoC), desktop computers, laptop computers, tablet computers, servers, smart phones, etc. Other example embodiments may be implemented as software executed by a programmable control device.

Care Protocol Modules

In some embodiments, each of the care protocol modules 102, 104, and 106 is configured to execute a particular patient care protocol. According to these embodiments, in executing a patient care protocol, a care protocol module executes a sequence of actions with defined transitions between a series of states. Thus, a care protocol module may implement a patient care protocol as a state machine with a series of logical tests. The sequence of actions executed by a care protocol module is defined within a set of instructions (e.g., the instructions 120, which are described further below). The sequence of actions may include actions such as connecting and communicating with other components, such as resource modules or other care protocol modules, for informational and control purposes. In this way, a care protocol module may activate or be activated by resource modules or other care protocol modules. Furthermore, a care protocol module may alter the patient care protocol that it executes based on information provided by a resource module or another care protocol module. Thus, a care protocol module may communicate and interoperate with a variety of components within a given medical device 100.

In some embodiments, the sequence of actions executed by a care protocol module may include, for example, registration of the care protocol module with resource modules or other care protocol modules to receive notifications. These notifications may be transmitted periodically, asynchronously, or in response to an occurrence of an event. In addition, a notification may be broadcast to multiple target components simultaneously where more than one component has registered for the notification. The information included in a notification may indicate state changes within the care protocol module, status of the patient care protocol being executed by the care protocol module, physiological data (e.g., heart rate data, pulse oximetry data, etc.), device status data (e.g., results of initialization tests, battery charge level, etc.), or other information.

Further, in some embodiments, a care protocol module is configured to utilize any service components, such as the service components 114 and 116, indirectly via a resource module associated with the common service component. In these embodiments, the patient care protocols executed by the care protocol modules are associated with a priority and a level of service. The priority indicates a level of importance of the patient care protocol with which it is associated. Protocol priorities may be used by resource modules to resolve conflicts between patient care protocols for common service components managed by the resource modules. The level of service indicates a level of performance that the patient care protocol requires of a resource module. In some embodiments, the instructions 120 executed by the care protocol module are configured to accommodate denied requests for utilization of the service components (e.g., when the common service component is already sufficiently utilized by another component with sufficient priority).

As shown in FIG. 1, each care protocol module includes data (e.g., the data 122) that is local to the care protocol module. In at least one embodiment, each care protocol module is configured to selectively prevent other components from accessing (e.g., reading or writing) its local data. In other embodiments, one or more care protocol modules are configured to completely bar other components from writing to local data, thereby making the local data completely private or otherwise inaccessible without some affirmative and informed grant of permission by the care protocol module.

With continued reference to FIG. 1, the illustrated elements of the care protocol module 102 will now be described. In some embodiments, the instructions 120 are configured to implement the patient care protocol executed by the care protocol module 102. The instructions 120 may specify, for instance, actions to manipulate data, perform calculations, transmit messages, register for notifications, and the like. For example, the instructions 120 may specify that the care protocol module 102 register for notifications from resource modules or other care protocol modules.

In other embodiments, the instructions 120 may specify that the care protocol module 102 reference one or more configuration options during module initialization and, where the configuration options indicate that the care protocol module 102 is blocked, terminate execution. These configuration options may be stored as one or more configurable parameters. In some embodiments, these configuration options may be altered during execution of the care protocol module 102 and thereby alter its operation. The instructions 120 may be encoded in some memory facility or otherwise accessible for execution by a hardware processor, virtual processor, translator, or other processing component. When executed in sequence, the instructions 120 cause the medical device 100 to execute a patient care protocol. A generalized example of a patient care protocol is described further below with reference to FIG. 6. Particular examples of patient care protocols are described further below with reference to FIGS. 7-9.

In some embodiments, the interface 118 includes a set of functions that enable the care protocol module 102 to interoperate with other components of the medical device 100, such as any of resource modules 108, 110, and 112, and the other care protocol modules 104 and 106. For example, in one embodiment, the interface 118 includes functions configured to transmit and receive requests, responses, notifications, and other messages in accord with the instructions 120. In this embodiment, a request transmitted via the interface 118 includes encoded data addressed to a target component. This encoded data may be, for instance, descriptive of an action requested by the care protocol module 102 for execution by the target component. For example, a subset of the instructions 120 may require that a particular alert be output via a user interface. The care protocol module 102 may implement this subset of the instructions 120 by transmitting a request to a resource module that manages the user interface with encoded data that specifies the alert.

In one embodiment, a request received by the interface 118 includes encoded data addressed to the care protocol module 102. This encoded data may be descriptive of an action requested by a given source component for execution by the care protocol module 102. In response to receiving a request, the care protocol module 102 executes a subset of the instructions 120 associated with the request, determines a result, and transmits a response with encoded data descriptive of the result to the source component via the interface 118. The result may include, for instance, state or status information, physiological data, device status data, care protocol module status data (e.g., data indicating the care protocol module is blocked), and data descriptive of components registered to receive information from the care protocol module. For example, the result may include state information descriptive of the current state of the resource module.

In some embodiments, the subset of the instructions may implement a registration process by which a given source component can register itself to receive notifications from the care protocol module 102. In response to receiving a request for registration, the care protocol module 102 may execute this subset of instructions. When executing the subset of instructions, the care protocol module 102 may store, in the data 122, an identifier of the source component and the type of notifications requested and may further transmit a response to the source component via the interface 118. The response may include encoded data that indicates successful registration of the source component with the care protocol module 102. In this example embodiment, notifications transmitted and received by the interface 118 are indirectly solicited or unsolicited messages that the care protocol module 102 processes in accord with the instructions 120. For example, notifications may be transmitted to target components in response to the care protocol module 102 detecting an event for which the target components are registered. Conversely, the interface 118 may receive notifications from source components with which the care protocol module 102 is registered to receive events. These notifications may include, for instance, encoded data identifying the event and information associated with the event (e.g., source, time, state change, data values, etc.).

In other embodiments, the data 122 is private information utilized by the care protocol module 102 in accord with the instructions 120 to execute a patient care protocol. As such, the data 122 may include a wide variety of temporary or permanent data values that describe characteristics of the care protocol module 102, the patient care protocol being executed by the care protocol module 102, or other system components with which the care protocol module 102 communicates.

Resource Modules

In some embodiments, each of the resource modules 108, 110, and 112 is configured to manage a common service component, such as one of the service components 114 and 116. According to these embodiments, in managing a common service component, a resource module executes actions defined within a set of instructions (e.g., the instructions 126, which are described further below). The actions may include, for instance, activating a common service component, allocating service components for use by care protocol modules, commanding the common service component to perform one or more functions or other processing, connecting and communicating with other components, such as care protocol modules or other resource modules, for informational and control purposes, and resolving contention between requests to utilize a common service component. In this way, a resource module may activate or be activated by care protocol modules or other resource modules. Furthermore, a resource module may alter how it manages a common service component based on information provided by a care protocol module or another resource module. Thus, a resource module may communicate and interoperate with a variety of components with a medical device.

In some embodiments, resource modules allocate capacity of service components and use the allocated capacity to process requests generated by care protocol modules that implement patient care protocols. In these embodiments, the patient care protocols and care protocol modules have associated levels of service and priorities. A level of service indicates a performance level (as may be measured, such as output volume rate, response time, etc.) that a care protocol module requires of a resource module. A level of service is used by the resource module to determine an amount of allocated capacity of the service component required to process requests from the care protocol module at the level of service demanded by the care protocol module. This allocation requirement may be expressed in absolute terms (e.g., units of service component output) or relative terms (e.g., percentage of service component capacity). For example, a resource module may translate a level of service required by a care protocol module to a number of DSP or other processor computing cycles and amount of memory required to perform at the performance level demanded by the level of service.

In some embodiments, priorities of patient care protocols and care protocol modules are used to detect and resolve conflicts for service components. In these embodiments, the instructions executed by a resource module are configured to detect a conflict where the level of service demanded by two or more care protocol modules cannot be provided by a service component. Further, in these embodiments, the instructions resolve contentious requests for a common service component managed by the resource module according to a resolution scheme. Examples of resolution schemes that may be implemented by a resource module include FIFO (in which requests are processed in the order in which they are received, also known as first in, first out), source component priority (e.g., requests generated by care protocol modules associated with a higher priority are processed first and requests generated by care protocol modules associated with a lower priority are either denied processing or processed after the other requests), and task priority.

In some embodiments, a resource module is not be the final arbiter of which requests from care protocol modules are processed by a service component. For example, in some embodiments, a conflict arbitration engine executes some or all the logic and computations to determine which requests to process where a resource module has determined that more than one care protocol module has communicated a request for processing by a particular service component. In some such embodiments, the resource module may transmit a request for arbitration to the conflict arbitration engine in response to receiving a request for a service component, as will now be discussed with reference to the example embodiment shown in FIG. 10.

Figure 10:
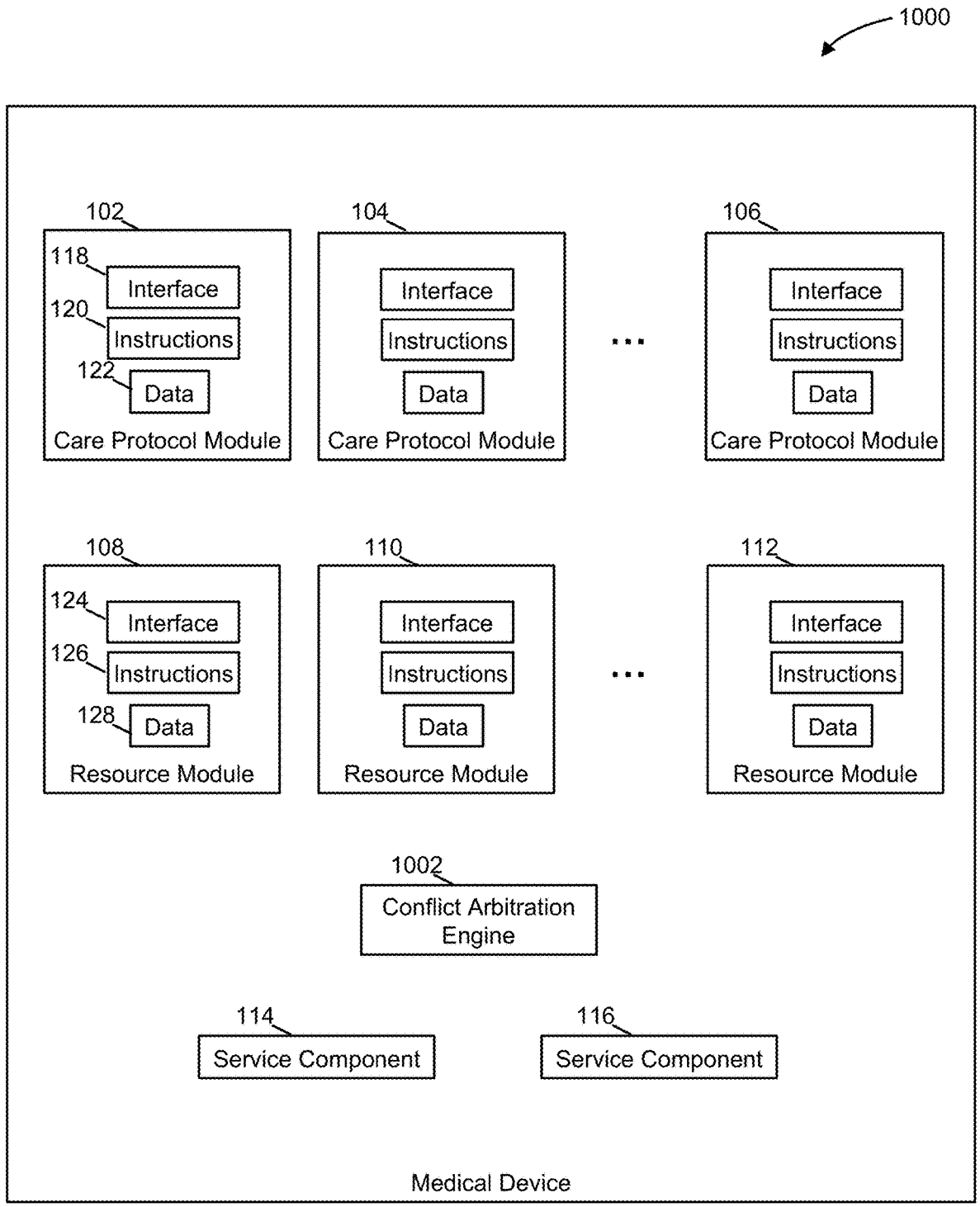
FIG. 10 illustrates another example medical device configured to execute multiple treatment protocols, in accordance with an embodiment of the present disclosure.

FIG. 10 illustrates an example medical device 1000 that includes components of the medical device 100 described above with reference to FIG. 1 and further includes a conflict arbitration engine 1002, according to another embodiment of the present disclosure. In the example medical device 1000, contentious requests for a common service component are arbitrated by the conflict arbitration engine 1002. In this example embodiment, the conflict arbitration engine 1002 compares all resource requests to a table of allowed resource state transitions. The conflict arbitration engine 1002 may execute rule-based decision logic to determine which requests are processed. For instance, the decision logic may be in the form of a prioritized case statement or may refer to a conflict resolution look-up table. In some embodiments, each resource module stores a minimum of one entry with an associated action for requests that are rejected. In one example, the conflict resolution table may be structured as shown in Table 1.

TABLE 1

Example Conflict Resolution Table

| Field | Description |
|---|---|
| Requestor ID | Unique identifier associated with a given source component (e.g., care protocol module, or other component initiating or otherwise sourcing a request) transmitting a request for processing by a service component. |
| Resource Name | The resource module addressed by the request |
| Priority | The priority of the source component |
| Current State | Current state of the resource module |
| Requested State or Action | The state change or action requested by the source component |
| Allowed Transitions | A list of states that may be transitioned to given the Current State |
| Action Function | A pointer to a function to be executed to change the Current State to the Requested State |

In some embodiments, the conflict arbitration engine 1002 is configured to evaluate the requested action using priority, current state, requested state, and allowed transitions. In some such embodiments, the conflict arbitration engine 1002 is also configured to execute the action function to implement the allowed transition.

In some embodiments, the conflict arbitration engine 1002 is further configured execute as follows. Responsive to determining that a requested state is not listed in the look-up table, the conflict arbitration engine 1002 may reject the request. Responsive to receiving a request from a source component with a lower priority than the priority of a source component associated with a request currently being processed by the service component, the conflict arbitration engine 1002 may reject the lower priority request. Responsive to receiving a request from a source component that is not recognized, the conflict arbitration engine 1002 may reject the unrecognized request. Where a rejection occurs, the conflict arbitration engine 1002 notifies the resource component, which in turn notifies the source component of the rejection. Responsive to receiving a request from a source component with a higher priority than the priority of a source component associated with a request currently being processed by the service component, the conflict arbitration engine 1002 may override the lower priority request. Where an override occurs, the conflict arbitration engine 1002 notifies the resource component, which in turn notifies the source component of the override.

In some embodiments, the conflict arbitration engine 1002 executes on the medical device 1000. However, in other embodiments, the conflict arbitration engine 1002 may execute on a local companion computing system communicatively coupled to the medical device 1000 via a LAN. In still other embodiments, the conflict arbitration engine 1002 may execute on a remote companion computing system communicatively coupled to the medical device 1000 via a WAN. As will be appreciated in light of this disclosure, relevant factors such as timing constraints and practicality may dictate that the best location for the conflict arbitration engine 1002 to execute is on the medical device 1000. But this need not be the case in all embodiments of the present disclosure.

Other functions may also be offloaded to a local companion computing system. For instance, in some cases, the display function may be offloaded to a local companion computing system. Other functions may include, for instance, communication network integrity checking (e.g., wireless network strength, available bandwidth, environmental analysis (e.g., ambient temperature), audio and video generation (e.g., for sending video of CPR being carried out on patient). Other functions that can be modularized or otherwise contained within a given routine will be apparent in light of this disclosure. If the communication link between the medical device and the companion computing system or service fails, the device can immediately revert to standalone mode to ensure continuity of care.

In some embodiments, service components may only be accessed via resource modules. For example, in one embodiment, only one resource module is capable of discharging a defibrillator. In other embodiments, resource modules may communicate and interoperate with other resource modules in a hierarchical manner, thereby completing complex tasks without exposing implementation details to care protocol modules. For example, a first resource module may sample a signal received from a sensor and store data descriptive of the signal, a second resource module may retrieve the stored data and analyze the signal to interpret its meaning, and a third resource module may be notified of an analysis result computed by the second resource module and, in response, take action.

In some embodiments, the actions executed by a resource module may include registration of the resource module with resource modules to receive notifications. These notifications may be transmitted periodically, asynchronously, or in response to an occurrence of an event. In addition, a notification may be broadcast to multiple target components simultaneously where more than one component has registered for the notification. The information included in notification may indicate state changes within the resource module, availability of the common service component managed by the resource module, physiological data, device status data, resource status data (e.g., data indicating the resource module is blocked), data descriptive of components registered to receive information from the resource module, or other information.

As further shown in FIG. 1, each resource module includes data (e.g., the data 128) that is local to the resource module. In at least one embodiment, each resource module is configured to selectively prevent other components from accessing (e.g., reading or writing) its local data. In other embodiments, one or more resource modules are configured to completely bar other components from writing to local data, thereby making the local data completely private. In at least one embodiment, some resource modules are configured to provide read-only access to trusted care protocol modules.

With continued reference to FIG. 1, the illustrated elements of the resource module 108 will now be discussed. In some embodiments, the instructions 126 are configured to implement management and control actions for a common service component and data analysis actions related to the common service component. The instructions 126 may specify actions to manipulate data, perform calculations, transmit messages, register for notifications, and the like. For example, the instructions may specify that the resource module 108 register for notifications from other resource modules. In at least one embodiment, however, the resource module 108 may not register for notifications from care protocol modules.

In other embodiments, the instructions 126 may specify that the resource module 108 reference one or more configuration options during module initialization and, where the configuration options indicate that the resource module 108 is blocked, terminate execution. These configuration options may be stored as one or more configurable parameters. In some embodiments, these configuration options may be altered during execution of the resource module 108 and thereby alter its operation. The instructions 126 may be encoded for execution by a hardware processor, virtual processor, translator, or other processing component. When executed in combination, the instructions 126 cause the medical device 100 to manage access to, and control processing of requests by, one or more service components. A generalized example of a resource management process is described further below with reference to FIG. 6. Particular examples of resource management processes are described further below with reference to FIGS. 7-9.

In some embodiments, the interface 124 includes a set of functions that enable the resource module 108 to interoperate with other components of the medical device 100, such as any of care protocol modules 102, 104, and 106, and the other resource modules 110 and 112. For example, in one embodiment, the interface 124 includes functions configured to transmit and receive requests, responses, notifications, and other messages in accord with the instructions 126. In this embodiment, a request transmitted via the interface 124 includes encoded data addressed to a target component. This encoded data may be descriptive of an action requested by the resource module 108 for execution by the target component. For example, a subset of the instructions 124 may require that an output request received from a care protocol module be executed. The resource module 108 may implement this subset by transmitting a request to the user interface with encoded data that specifies the output.

In one embodiment, a request received by the interface 124 includes encoded data addressed to the resource module 108. This encoded data may be descriptive of an action requested by a given source component for execution by the resource module 108. In response to receiving a request, the resource module 108 executes a subset of the instructions 126 associated with the request, determines a result, and transmits a response with encoded data descriptive of the result to the source component via the interface 124. The result may include data, state, or status information. For example, the result may include state information descriptive of the current state of the resource module. In some embodiments, the subset of the instructions may implement a registration process by which a source component can register itself to receive notifications from the resource module 108. In response to receiving a request for registration, the resource module 108 may execute this subset of instructions. When executing the subset of instructions, the resource module 108 may store, in the data 128, an identifier of the source component and the type of notifications requested and may further transmit a response to the source component via the interface 126. The response may include encoded data that indicates successful registration of the source component with the resource module 108.

In this embodiment, notifications transmitted and received by the interface 124 are indirectly solicited or unsolicited messages that the resource module 108 processes in accord with the instructions 126. For example, notifications may be transmitted to target components in response to the resource module 108 detecting an event for which the target components are registered. Conversely, the interface 124 may receive notifications from source components with which the resource module 108 is registered to receive events. These notifications may include encoded data identifying the event and information associated with the event (e.g., source, time, state change, data values, etc.).

In other embodiments, the data 128 is private information utilized by the resource module 108 in accord with the instructions 126 to manage a common resource. As such, the data 128 may include a wide variety of temporary or permanent data values that describe characteristics of the resource module 108, the management processes being executed by the resource module 102, or other system components with which the resource module 108 communicates.

Medical Device Controller

Figure 2:
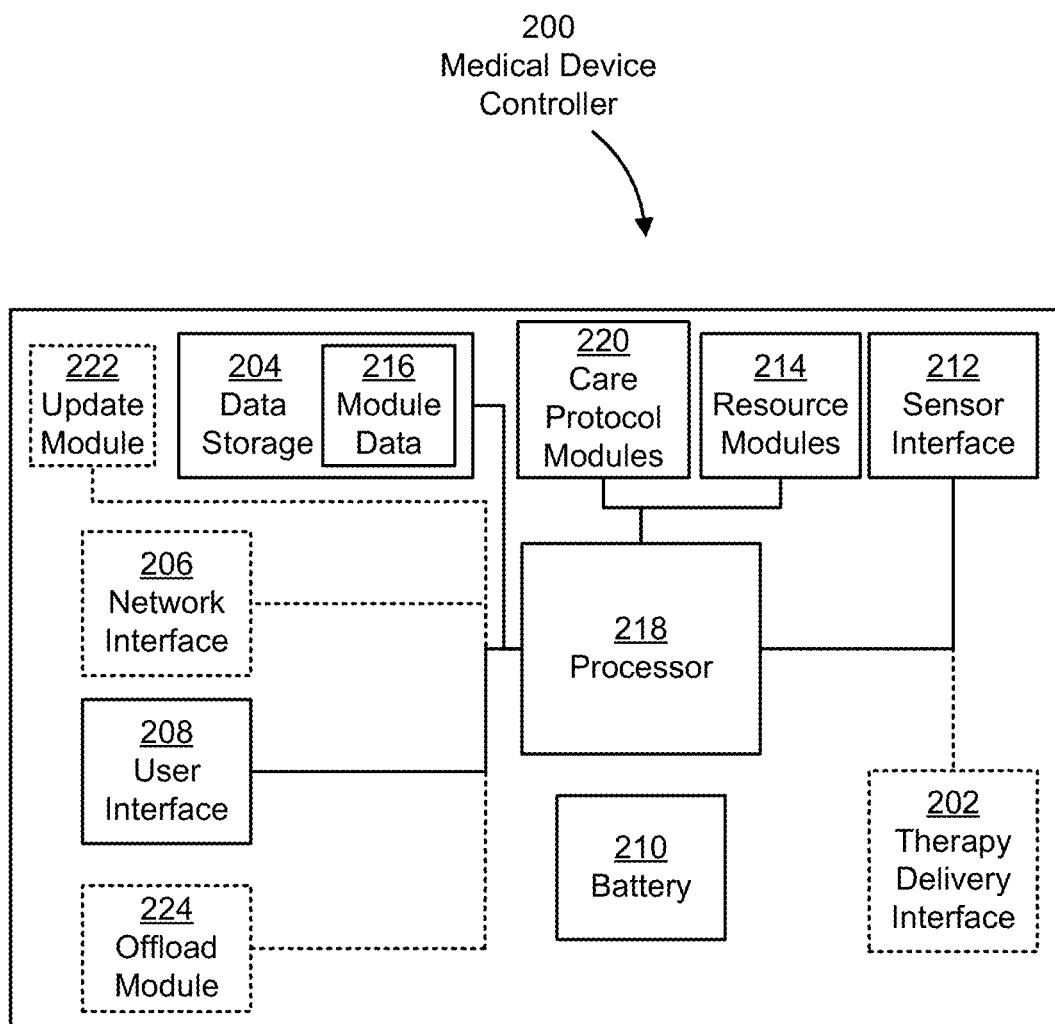
FIG. 2 is a functional schematic of an example medical device controller configured in accordance with an embodiment of the present disclosure.

FIG. 2 illustrates a medical device controller 200 that is configured to monitor a patient and the patient's environment for events of interest, via execution of care protocol modules and resource modules. The medical device controller 200 may, for example, be configured for use in a wearable defibrillator or an Automated External Defibrillator (AED) As shown in FIG. 2, the medical device controller 200 includes a processor 218, a sensor interface 212, care protocol modules 220, resource modules 214, an update module 222, a therapy delivery interface 202, data storage 204, a communication network interface 206, a user interface 208, an offload module 224, and a battery 210. The data storage 204 includes module data 216. Further, in one such example embodiment, the battery 210 is a rechargeable 3-cell 2200 mAh lithium ion battery pack that provides electrical power to the other device components with a minimum 24 hour runtime between charges. It will be appreciated, however, that such features as battery capacity, runtime, and type (e.g., lithium ion, nickel-cadmium, or nickel-metal hydride) may be changed to best fit the specific application of the medical device controller 200. Any number of suitable battery technologies can be used.

According to the embodiment illustrated in FIG. 2, the processor 218 is coupled to the sensor interface 212, the therapy delivery interface 202, the data storage 204, the network interface 206, and the user interface 208. The processor 218 performs a series of instructions that result in manipulated data which are stored in and retrieved from the data storage 204. According to some embodiments, the processor 218 is a commercially available processor such as a processor manufactured by Texas Instruments, Intel, AMD, Sun, IBM, Motorola, Freescale, and ARM Holdings. However, the processor 218 may be any type of processor, multiprocessor or controller, whether commercially available or specially manufactured. For instance, according to one embodiment, the processor 218 may include a power conserving processor arrangement such as the arrangement described in U.S. Pat. No. 8,904,214, titled System and Method for Conserving Power in a Medical Device, issued Dec. 2, 2014 (hereinafter the '214 patent), which is herein incorporated by reference in its entirety. In another embodiment, the processor 218 is an Intel® PXA270.

In addition, in some embodiments the processor 218 is configured to execute a conventional real-time operating system (RTOS), such as RTLinux. In these embodiments, the RTOS may provide platform services to application software, such as some embodiments of the care protocol modules 220 and resource modules 214 described below. These platform services may include inter-process and network communication, file system management and standard database manipulation. One or more of many operating systems may be used, and embodiments are not limited to any particular operating system or operating system characteristic. For instance, in some embodiments, the processor 218 may be configured to execute a non-real-time operating system, such as BSD or GNU/Linux.

In some embodiments, the care protocol modules 220 and the resource modules 214 are configured to drive operation of the medical device. Particular examples of the processes performed by the care protocol modules 220 and the resource modules 214 are discussed further below with reference to FIGS. 7-9.

In some embodiments, the update module 222 is configured to update the care protocol modules 220 and the resource modules 214. The update module 222 may update the care protocol modules 220 independently from one another and independently from the resource modules 214 because of the loosely coupled implementation of these components. The update module 222 may also update the resource modules 214 independently from one another and independently from the care protocol modules 220.

The care protocol modules 220 and the resource modules 214 may be implemented using hardware or a combination of hardware and software. For instance, in one embodiment, the care protocol modules 220 and the resource modules 214 are implemented as software components that are stored within the data storage 212 and executed by the processor 218. In this embodiment, the instructions included in the care protocol modules 220 and the resource modules 214 program the processor 218 to drive operation of the medical device. In other embodiments, the care protocol modules 220 and the resource modules 214 may be, for example, application-specific integrated circuits (ASICs) that are coupled to the processor 218 and tailored to drive the operation of the medical device, under the control or direction of processor 218. Thus, examples of the care protocol modules 220 and the resource modules 214 are not limited to a particular hardware or software implementation.

In some embodiments, the components disclosed herein, such as the care protocol modules 220 and the resource modules 214, may read parameters that affect the functions performed by the components. These parameters may be physically stored in any form of suitable memory including volatile memory, such as RAM, or nonvolatile memory, such as a flash memory or magnetic hard drive or ROM. In addition, the parameters may be logically stored in a propriety data structure, such as a database or file defined by a user mode application, or in a commonly shared data structure, such as an application registry that is defined by an operating system. In addition, some embodiments provide for both system and user interfaces, as may be implemented using the user interface 208, that allow external entities to modify the parameters and thereby configure the behavior of the components.

The data storage 204 includes a computer readable and writeable nonvolatile data storage medium configured to store non-transitory instructions and data. In addition, the data storage 204 includes processor memory that stores data during operation of the processor 218. In some embodiments, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several embodiments, the processor 218 causes data to be read from the nonvolatile data storage medium into the processor memory prior to processing the data. In these embodiments, the processor 218 copies the data from the processor memory to the non-volatile storage medium after processing is complete. A variety of components may manage data movement between the non-volatile storage medium and the processor memory and embodiments are not limited to particular data management components. Further, embodiments are not limited to a particular memory, memory system or data storage system.

The instructions stored on the data storage 204 may include executable programs or other code that can be executed by the processor 218. The instructions may be persistently stored as encoded signals, and the instructions may cause the processor 218 to perform the functions described herein. The data storage 204 also may include information that is recorded, on or in, the medium, and this information may be processed by the processor 218 during execution of instructions. The medium may, for example, be optical disk, magnetic disk or flash memory, among others, and may be permanently affixed to, or removable from, the medical device controller 200.

In some embodiments, the module data 216 includes data used by the care protocol modules 220 and the resource modules 214 to drive operation of the medical device. More particularly, according to the illustrated embodiment, the module data 216 includes information that identifies and implements the resource modules 214, care protocol modules 220, software implemented service components. The module data 216 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various embodiments organize the module data 216 into particularized and, in some cases, unique structures to perform the functions disclosed herein. In these embodiments, the data structures are sized and arranged to store values for particular types of data, such as integers, floating point numbers, character strings, arrays, linked lists, and the like.

As shown in FIG. 2, the medical device controller 200 includes several system interface components 202, 206, and 212. Each of these system interface components is configured to exchange, i.e. send and/or receive, data with one or more specialized devices or systems that may be located within the housing of the medical device controller 200 or elsewhere. The components used by the interfaces 202, 206, and 212 may include hardware components, software components or a combination of both. Within each interface, these components physically and logically couple the medical device controller 200 to the specialized devices/systems. This physical and logical coupling enables the medical device controller 200 to both communicate with and, in some instances, power or control the operation of the specialized devices/systems. These specialized devices/systems may include, for example, physiological sensors, therapy delivery devices, computer networking devices, and companion computing systems, either local or remote. As previously explained, such a companion computing system (e.g., local tablet computer or remote cloud-based service)

can be used, for example, to carry out certain functions as directed by the medical device controller 200, or some other controlling entity.

According to various embodiments, the hardware and software components of the interfaces 202, 206 and 212 implement a variety of coupling and communication techniques. In some embodiments, the interfaces 202, 206, and 212 use leads, cables or other wired connectors as conduits to exchange data between the medical device controller 200 and specialized devices. In other embodiments, the interfaces 202, 206, and 212 communicate with specialized devices using wireless technologies such as radio frequency or infrared technology (e.g., Wi-Fi or Bluetooth communication links). The software components included in the interfaces 202, 206, and 212 enable the processor 218 to communicate with specialized devices. These software components may include elements such as objects, executable code, and populated data structures. Together, these software components provide software interfaces through which the processor 218 can exchange information with specialized devices. Moreover, in at least some embodiments where one or more specialized devices communicate using analog signals, the interfaces 202, 206, and 212 further include components configured to convert analog information into digital information, and vice versa, to enable the processor 218 to communicate with specialized devices.

As discussed above, the system interface components 202, 206, and 212 shown in the example embodiment of FIG. 2 support different types of specialized devices. For instance, the components of the sensor interface 212 couple the processor 218 to one or more physiological sensors such as a body temperature sensors, respiration monitors, oxygen level sensors, patient impedance sensors, and electrocardiogram (ECG) sensing electrodes. Other sensors may include, for instance, one or more environmental sensors such as atmospheric thermometers, airflow sensors, video sensors, audio sensors, accelerometers, GPS locators, and hygrometers. In these embodiments, the sensors may include sensors with a relatively low sampling rate, such as wireless sensors. In a more general sense, the sensors may be for detecting any target parameter to be monitored and may have any sampling rate suitable for the intended application.

The components of the therapy delivery interface 202 couple one or more therapy delivery devices, such as capacitors, defibrillator electrodes, pacing electrodes, or mechanical chest compression devices, to the processor 218. It will be appreciated that the functionality of the therapy delivery interface 202 may be incorporated into the sensor interface 212 to form a single interface coupled to the processor 218. As further illustrated in FIG. 2 by virtue of dashed line, note that the therapy delivery interface 202 is optional and may not be included in every embodiment. For instance, a heart rate monitor may employ the medical device controller 200 to issue alarms but may not include a therapy delivery interface 202 to treat cardiac abnormalities.

In addition, the components of the network interface 206 can be used couple the processor 218 to a computer network via a networking device, such as a bridge, router or hub, or even a mobile telephone configured with networking technology and integrated within or otherwise operatively coupled with the medical device controller 200. According to a variety of embodiments, the network interface 206 supports a variety of standards and protocols, examples of which include USB (via, for example, a dongle to a computer), TCP/IP, Ethernet, Wireless Ethernet, Bluetooth, Zig-Bee, M-Bus, CAN-bus, IP, IPV6, UDP, DTN, HTTP, FTP, SNMP, CDMA, NMEA and GSM. It will be further appreciated that the network interface 206 of medical device controller 200 may enable communication between other medical device controllers within a certain range or otherwise accessible by the network to which interface 206 can connect (much like a mobile computing device such as a smartphone or tablet can access a wireless local area network). As further illustrated in FIG. 2, the network interface 206 is optional and may not be included in every embodiment. For instance, an ambulatory defibrillator may include the medical device controller 200 to provide alarm functionality but may not include a network interface 206 where, for example, the ambulatory defibrillator is designed to rely on the user interface 208 to announce alarms, or other such use cases where the medical device controller 200 need not access componentry outside of the medical device controller 200.

Further note that the network accessible by the interface 206 may be a wired and/or wireless LAN that provides access to local devices on that LAN, but may also include or otherwise be coupled with a wide area network (WAN) such as a campus-wide network or a company-wide network and/or the Internet, so as to provide access to devices at any number of remote locations. In some embodiments, for example, network interface 206 can be used to access a local computing device to which at least some processing of the medical device controller 200 can be offloaded (by operation of the optional offload module 224). The local computing device may be, for instance, a tablet, smartphone, laptop, dedicated supplementary or supporting medical device, or some other computing system programmed to be a companion system to the controller 200. In some such example cases, any one or more of the care protocol modules 220 and/or the resource modules 214 can be offloaded to the computing device, once that device is authenticated by the offload module 224, as will be explained in turn. In still other embodiments, network interface 206 can be used to access a cloud-based service or other remote computing system that is programmed to, for example, receive patient data from the medical device controller 200 and provide medical guidance responsive to that data so as to assist in use of the medical device. Thus, in some embodiments, controller 200 is configured to offload processing to at least one of a local and remote processing facility, so as to assist in operation of the medical device.

To ensure data transfer is secure, in some embodiments, the medical device controller 200 can transmit data via the network interface 206 using a variety of security measures including, for example, TLS, SSL or VPN. In other embodiments, the network interface 206 includes both a physical interface configured for wireless communication and a physical interface configured for wired communication. According to still other various embodiments, the network interface 206 enables communication between the medical device controller 200 and a variety of other personal electronic devices and peripherals including computer enabled glasses and earpieces.

In one embodiment, the network interface 206 is also capable of transmitting or receiving information to assist in locating the medical device. This may be accomplished through one or more antennas integrated with or coupled to the network interface 206, and consequently coupled to the processor 218. For example, the one or more antennas may receive GPS signals from satellites. The GPS signals may be used to determine the location of the medical device with a given level of accuracy or used to determine the current time. It will be appreciated that the systems described above with regard to connecting to various networks (e.g., wireless Ethernet, Bluetooth, and/or Internet) may be used as probes to find predefined reference points within a given range. For example, the medical device controller 200 may detect a WLAN access point or a Bluetooth source. Additionally, in at least some embodiments, the network interface 206 may transmit notifications to remote devices in response to actions executed by a resource module managing or otherwise communicating through the network interface 206. Thus, the various system interfaces incorporated in the medical device controller 200 allow the medical device to interoperate with a wide variety of other devices (medical and non-medical) in various contexts. For instance, some embodiments of the medical device controller 200 are configured to perform a process of sending critical events and data to a centralized server or remote monitoring service via the network interface 206. Healthcare professionals can then review that data (either at the remote location, or elsewhere) and treat or otherwise work with the patient or a patient caregiver. Further details of one such example process in accord with these embodiments is disclosed in U.S. Pat. No. 6,681,003, titled "Data Collection and System Management for Patient-Worn Medical Devices," issued on Jan. 20, 2004, which is herein incorporated by reference in its entirety.

The user interface 208 shown in FIG. 2 includes a combination of hardware and software components that allow the medical device controller 200 to communicate with an external entity, such as a patient, healthcare provider, or other user. These components may be configured to receive information from actions such as physical gestures or movement, verbal intonation or thought processes from a given user (e.g., by way of a touch screen, camera, microphone, and/or brain-computer interface). In addition, the components of the user interface 208 can provide information to users (e.g., by way of a speaker, display, and/or haptic response). Examples of the components that may be employed in conjunction with the user interface 208 include keyboards, mouse devices, trackballs, microphones, electrodes, touch screens, printing devices, display screens, haptic transducers, and speakers. In some embodiments, the electrodes include an illuminating element, such as an LED. In other embodiments, the printing devices include printers (or other output devices) capable of rendering visual or tactile (Braille) output. In a more general sense, any suitable input/output mechanism can be used to allow for interaction with a medical device as provided herein.

In some embodiments, the offload module 224 is programmed or otherwise configured to detect the presence of, and validate, a companion system to which modular functionality can be offloaded for execution, such as care protocol modules 220 and/or resource modules 214. Such offloading may be beneficial, in that the medical device may be implemented in a relatively inexpensive way and still provide its core mission critical functionality. In addition, such offloading allows the medical device to conserve its resources, and the companion system may actually provide better performance or a richer feature set, such as a better display or processing power. As further seen in FIG. 2, the offload module 224 is communicatively coupled with the network interface 206. In such embodiments, the offload module 224 is programmed or otherwise configured to determine when a communication link (wired or wireless) is available, and to establish communication with potential companion systems via that link and to authenticate those systems.

Once a companion system is engaged and validated, the offload module 224 may offload the performance of one or more modular functions to that system. The modules to be offloaded can be determined in a number of ways. In some embodiments, for instance, the offload module 224 includes a table or other listing of functional modules that can be exported for execution by a companion system when a communication link is available and a given companion system properly validates. In some cases, the offload module 224 may only offload care protocol modules 220, while in other embodiments the offload module 224 may only offload resource modules 214. In still other embodiments, a mix of care protocol modules 220 and resource modules 214 may be approved for offloading. As will be appreciated, an existing regulatory framework may not allow or otherwise restrict offloading certain functionalities from a given medical device. In such cases, that particular restricted functionality need not be offloaded. In still other embodiments, note that the modules themselves can be designated as being candidates for offloading. For instance, the instructions 120 and/or data 122 of the care protocol modules may be configured with a settable flag or parameter or otherwise indicate whether that specific care protocol module can be offloaded. In a similar fashion, the instructions 126 and/or data 128 of the resource modules may be configured to indicate whether that specific resource module can be offloaded.

In some cases, the offload module 224 is configured to automatically offload any approved modular functions once a companion system is validated. In other embodiments, the offload module 224 is configured to offload approved modular functions once a companion system is validated, only when a computing burden threshold of the controller 200 is exceeded (e.g., such as when usage of processor 218 exceeds 50% of maximum processing capacity). In still other embodiments, the offload module 224 is configured to offload approved modular functions once a companion system is validated, in response to certain patient data being received (e.g., a medical condition requiring immediate intervention by a trained professional at a remote location). Numerous other use cases and variations will be appreciated in light of this disclosure.

Figure 14A:
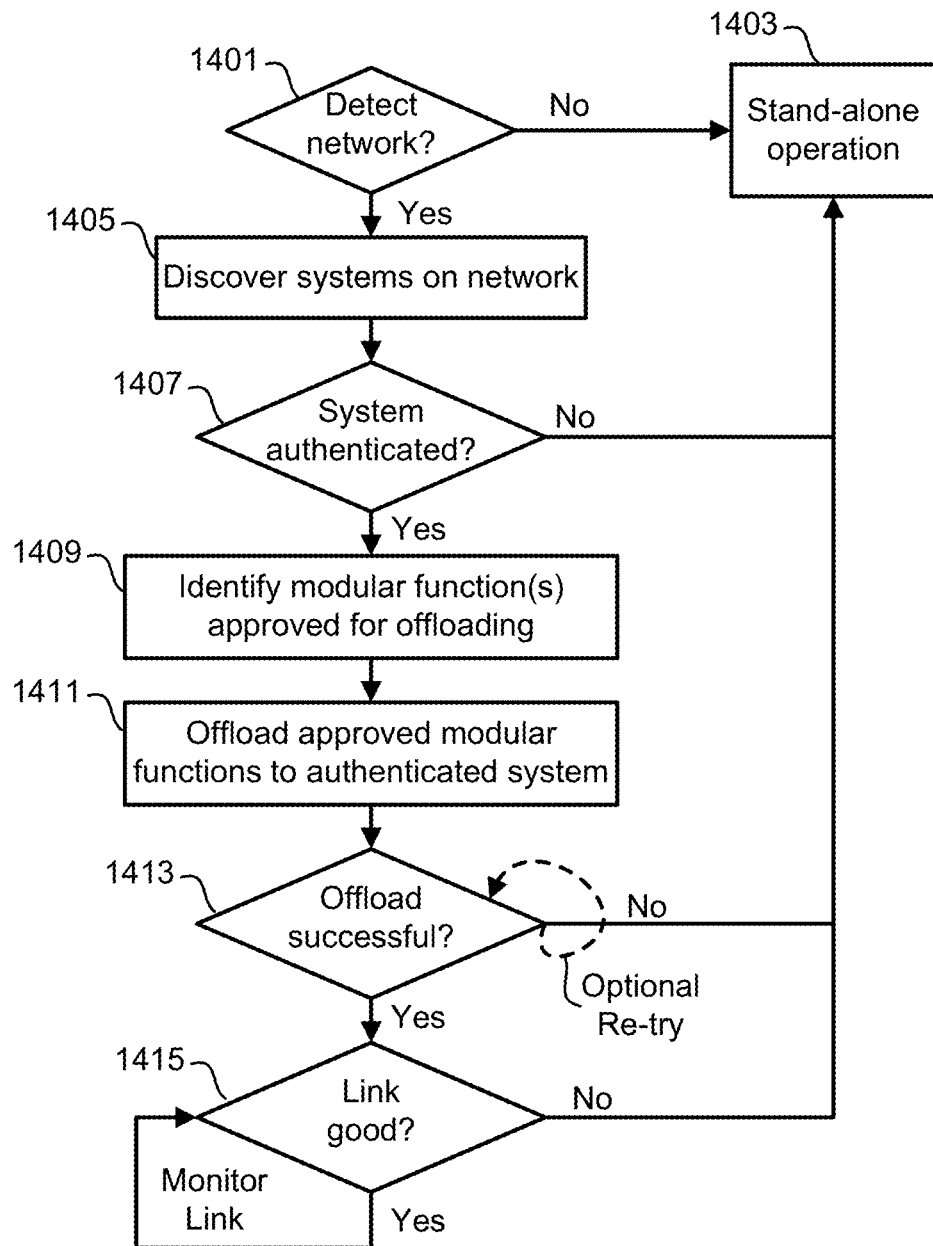
FIG. 14A illustrates a methodology for offloading select modular functions from a medical device to a companion computing system or service, in accordance with an embodiment of the present disclosure.
Figure 14B:
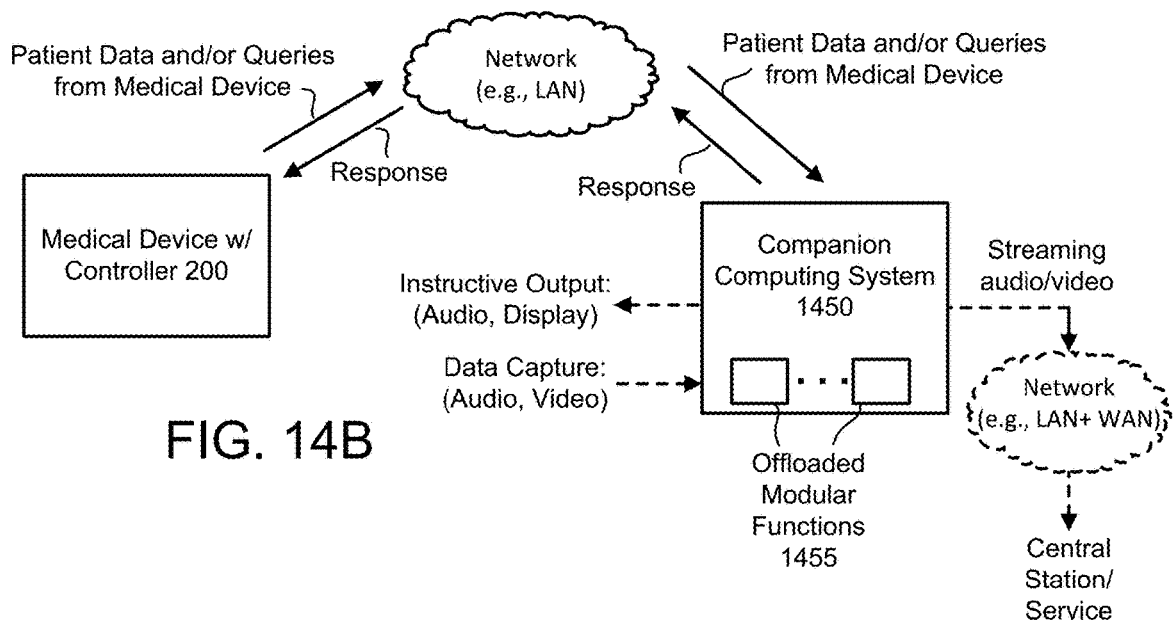
FIG. 14B illustrates a system for offloading select modular functions from a medical device to a companion computing system or service, in accordance with an embodiment of the present disclosure.
Figure 14C:
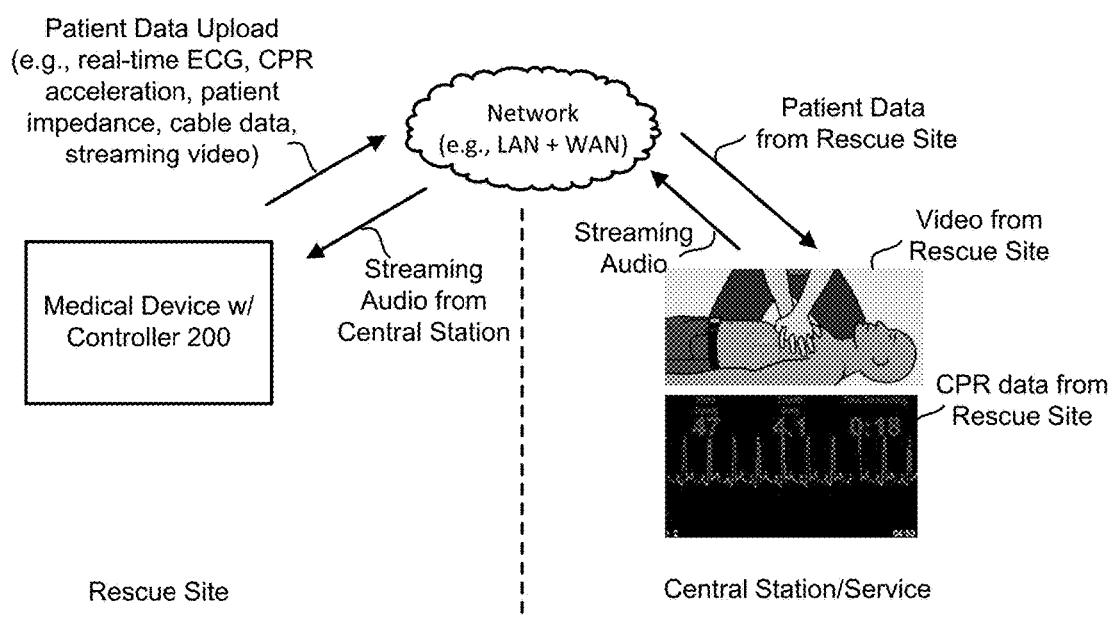
FIG. 14C illustrates a system for offloading select modular functions from a medical device to a companion computing system or service, in accordance with another embodiment of the present disclosure.

As further illustrated in FIG. 2, the offload module 224 is optional and may not be included in every embodiment. For instance, offloading of modular functionality need not be performed, as the medical device can be configured as a stand-alone system that needs no supplementary companion system to be fully operational. FIGS. 14A-C illustrate further details with respect to selectively offloading modular functionality, according to some embodiments, and will be discussed in turn.

The medical device controller 200 has a variety of potential applications and is well-suited to devices that notify external entities of a variety of events, some of which may require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the medical device controller 200 is well-suited include critical care medical devices, such as a wearable ambulatory external defibrillator, an AED, or a mechanical chest compression device, such as the Autopulse® system from ZOLL® Medical Corporation of Chelmsford, Mass.

Example Ambulatory Medical Device

Figure 3:
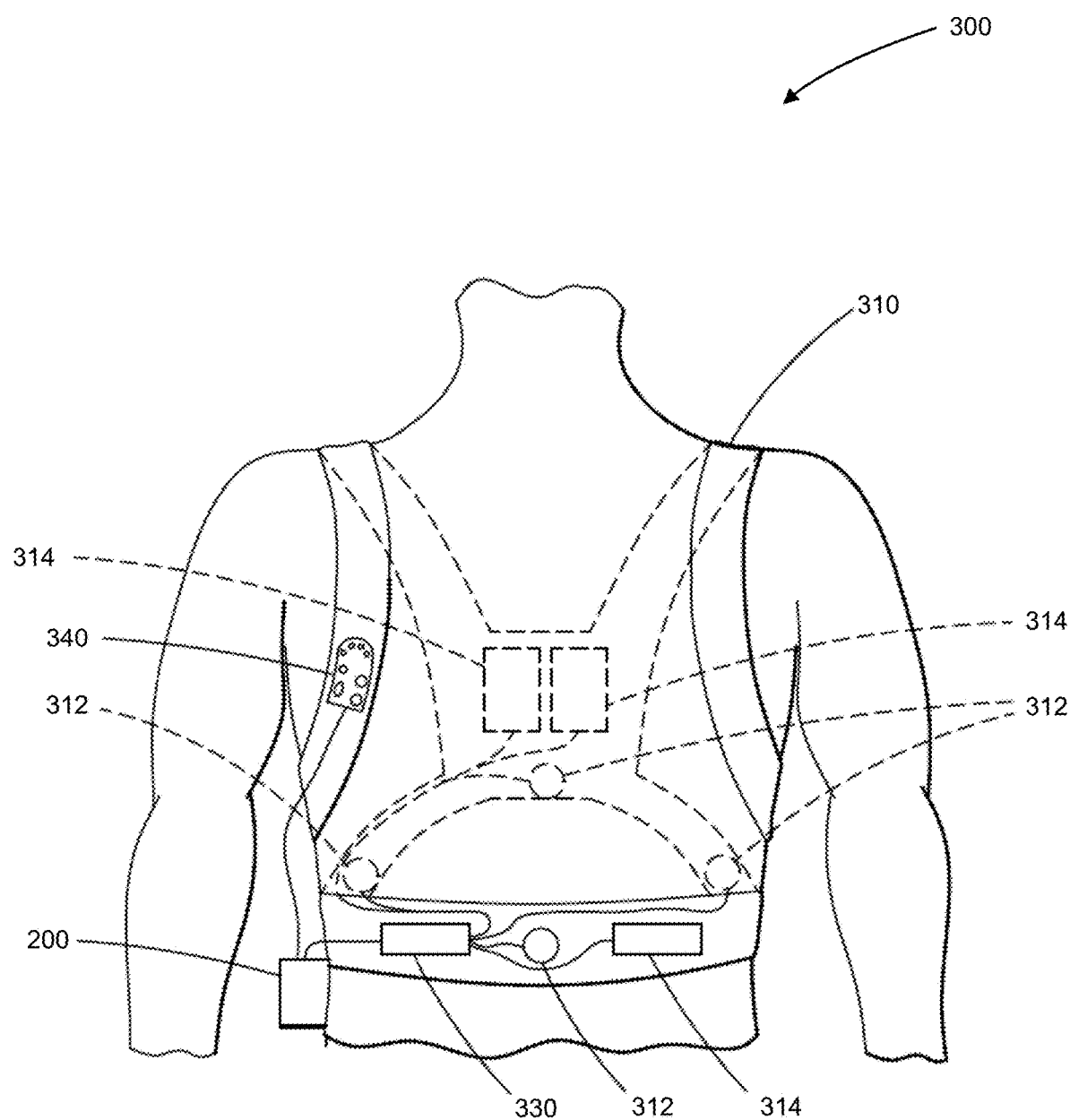
FIG. 3 illustrates an example ambulatory external medical device configured in accordance with an embodiment of the present disclosure.

In one embodiment, the medical device is a wearable defibrillator that includes a garment (e.g., a vest or belt) that is worn by the patient. The wearable defibrillator monitors the patient's ECG with sensing electrodes, detects life-threatening arrhythmias, and delivers a cardioverting or defibrillating shock through the therapy pads if treatment is necessary. FIG. 3 illustrates a wearable defibrillator, such as a LifeVest® wearable cardioverter defibrillator available from ZOLL® Medical Corporation. As shown, the wearable defibrillator 300 includes a harness 310 having a pair of shoulder straps and a belt that is worn about the torso of a patient. The wearable defibrillator 300 includes a plurality of ECG sensing electrodes 312 that are attached to the harness 310 at various positions about the patient's body and electrically coupled to the sensor interface 212 of the medical device controller 200 via a connection pod 330. The plurality of ECG sensing electrodes 312, which may be dry-sensing capacitance electrodes although any suitable ECG sensing electrode can be used, are coupled to the medical device controller 200 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 312 may be disposed at varying locations about the patient's body.

The wearable defibrillator 300 also includes a plurality of therapy electrodes 314 that are electrically coupled to the medical device controller 200 via the connection pod 330 and which are configured to deliver one or more therapeutic defibrillating shocks to the body of the patient, if it is determined that such treatment is warranted. The connection pod 330 electrically couples the plurality of ECG sensing electrodes 312 and the plurality of therapy electrodes 314 to the therapy delivery interface 202 of the medical device controller 200, and may include electronic circuitry. The connection pod 330 may also include other electronic circuitry, such as a motion sensor or accelerometer through which patient activity may be monitored.

As further shown in FIG. 3, the wearable defibrillator 300 also includes a user interface pod 340 that is electrically coupled to, or integrated in with, the user interface 208 of the medical device controller 200. The user interface pod 340 can be attached to the patient's clothing or to the harness 310, for example, via a clip (not shown) that is attached to a portion of the interface pod 340. Alternatively, the user interface pod 340 may simply be held in a person's hand. In some embodiments, the user interface pod 340 may communicate wirelessly with the user interface 208 of the medical device controller 200, for example, using a Bluetooth®, Wireless USB, ZigBee, Wireless Ethernet, GSM, or other type of communication interface.

The user interface pod 340 includes a number of buttons by which the patient, or a bystander can communicate with the medical device controller 200, and a speaker by which the medical device controller 200 may communicate with the patient or the bystander. For example, where the medical device controller 200 determines that the patient is experiencing cardiac arrhythmia, the medical device controller 200 may issue an audible alarm via a speaker on the medical device controller 200 or the user interface pod 340 alerting the patient and any bystanders to the patient's medical condition. The medical device controller 200 may also instruct the patient to press and hold one or more buttons on the user interface 208 of the medical device controller 200 or on the user interface pod 340 to indicate that the patient is conscious, thereby instructing the medical device controller 200 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

Figure 4B:
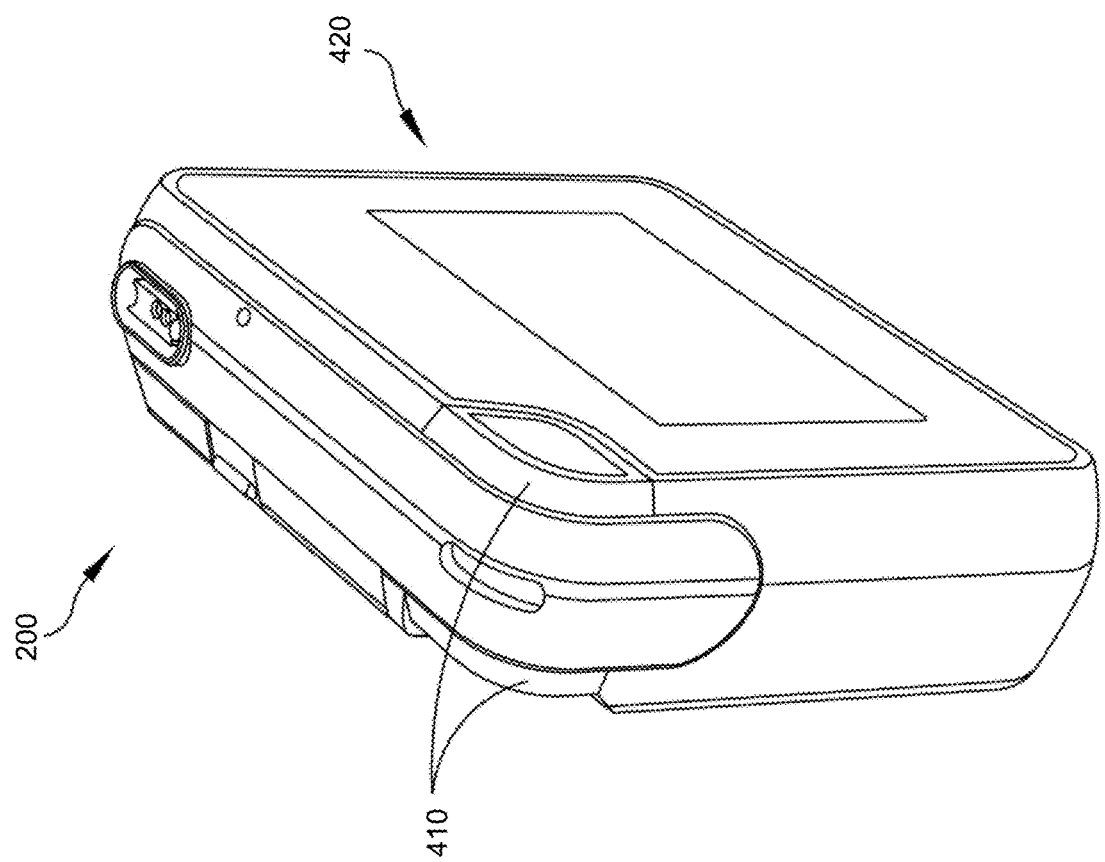
FIGS. 4A-B illustrate an example medical device controller for an ambulatory medical device, such as the example one shown in FIG. 3, configured in accordance with an embodiment of the present disclosure.
Figure 4A:
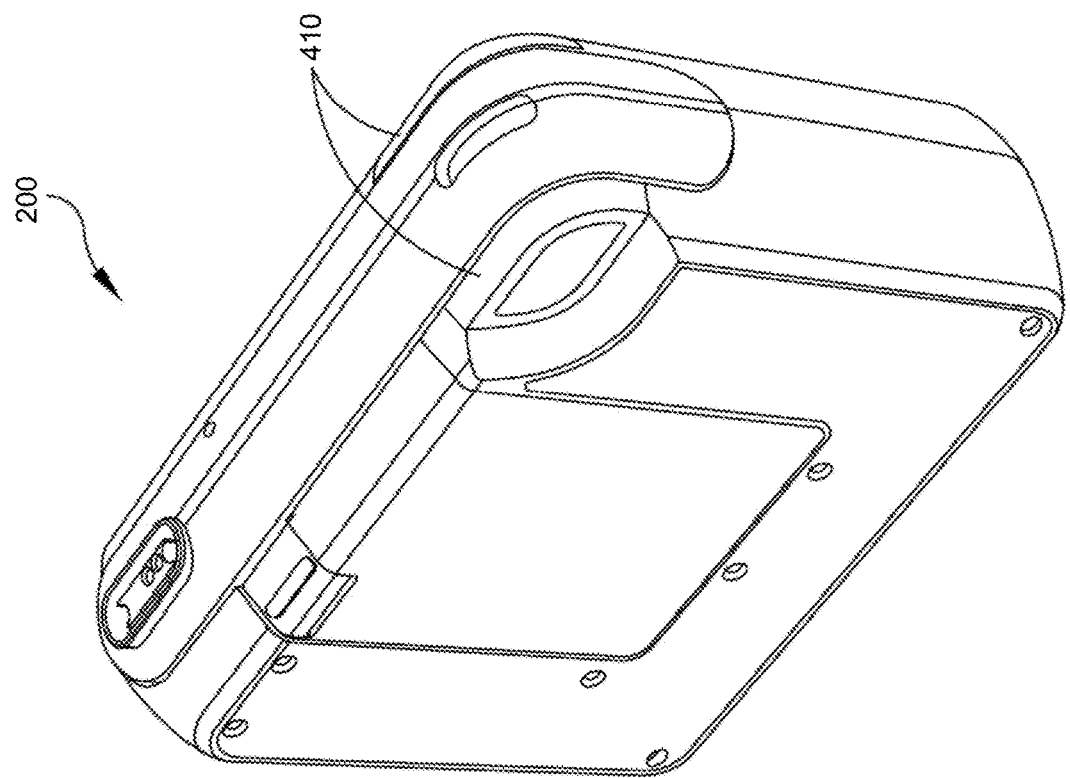

In another embodiment, the functionality of the user interface pod 340 is integrated into the housing of the ambulatory medical device controller 200. FIGS. 4A-B illustrate such an example of the ambulatory medical device controller 200. The ambulatory medical device controller 200 includes two response buttons 410 on opposing sides of the housing of the ambulatory medical device controller 200. As shown in FIGS. 4A-B, the response buttons 410 are recessed to reduce the likelihood of accidental activation (e.g., a patient falling on the response button). The ambulatory medical device controller 200 also includes, in this embodiment, a display screen 420 and a speaker to enable the communication of audible and visual stimuli to the patient. It will be appreciated that the response buttons 410 do not have to be placed on opposing sides of the housing as illustrated in FIGS. 4A-B. The response buttons, for example, may be located adjacent to each other in the housing the ambulatory medical device controller. The adjacent placement of the response buttons may make it easier for individuals with smaller hands or less dexterity to engage the response buttons.

Another example of a medical device is the ambulatory external defibrillator described in FIG. 3 of the previously incorporated '214 patent. In at least one embodiment of the present disclosure, the ambulatory defibrillator 300 illustrated in FIG. 3 of the '214 patent may employ the medical device controller 200, as a substitute for the portable treatment controller 200 described in the '214 patent. In such an embodiment, the ECG Electrodes and Therapy Pads illustrated in FIG. 3 of the '214 patent may be logically and physically coupled to the medical device controller 200 via the sensor interface 212 and the therapy delivery interface 202, respectively. While some of the embodiments disclosed herein are directed to medical device controllers in wearable ambulatory medical devices, the medical device controller 200 is well suited for other medical devices including other types of AEDs, implanted medical devices, and other medical devices configured to monitor, diagnose, and treat a given medical condition of a patient.

Example Automated Medical Device

Figure 5:
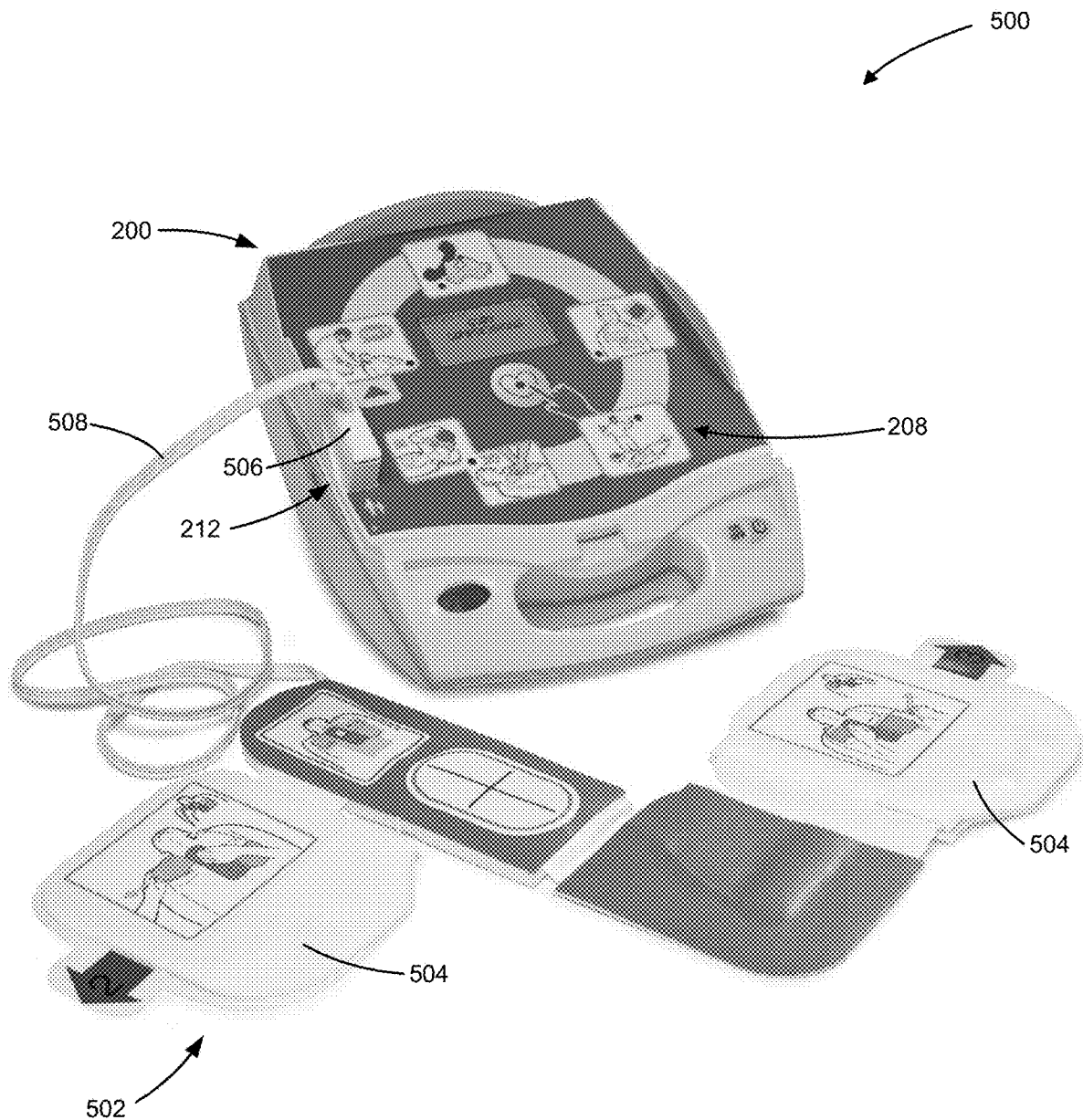
FIG. 5 illustrates another example of an external medical device having a controller configured in accordance with an embodiment of the present disclosure.

In one embodiment, the medical device is an AED. As previously explained, AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiopulmonary resuscitation (CPR). FIG. 5 illustrates an example AED, such as an AED Plus® automated external defibrillator available from ZOLL® Medical Corporation. As shown, the AED 500 includes a medical device controller 200 and an electrode assembly 502. The electrode assembly 502 includes one or more sensing electrodes 504 (e.g., ECG sensors), one or more therapy electrodes 504 (e.g., defibrillation pads), a connector 506, wiring 508 electrically coupling the connector 506 to the one or more sensing electrodes 504 and one or more therapy electrodes 504. As shown in FIG. 5, the connector is configured to couple the electrode assembly 502 to the medical device controller 200 and, more specifically, the one or more sensing electrodes to the sensor interface 212 and the one or more therapy electrodes to the therapy delivery interface 202.

The medical device controller 200 of the AED 500 is configured to detect the cardiac rhythm of the patient and provide defibrillating shocks to the patient as appropriate. This process is similar to the process described with regard to medical device controller 200 of the ambulatory medical device 300, and both such controllers 200 may be implemented according to an embodiment of the present disclosure. The user interface 208 of the AED 500 may include a variety of components configured to communicate with the operator including, but not limited to, a display screen, a speaker, and one or more buttons. In this embodiment, the AED 500 includes a display screen to display notifications to an operator. The notifications may provide instructions to the operator regarding the proper administration of CPR to the patient. The notifications on the display may be accompanied by audible alerts from the speaker to further assist the operator in administering CPR to the patient. According to various embodiments, the AED 500 and the wearable defibrillator 300 utilize the network interface 206 of the medical device controller 200 to determine location information and transmit the location information to the appropriate medical personnel. While some of the embodiments disclosed herein are directed to medical devices for cardiac monitoring and treatment, other embodiments are directed to other types of medical devices that compute their location through a variety of processes executed by the medical device controller 200.

Patient Care Protocols and Resource Management Processes

As can be seen in each of FIGS. 6 through 9, the various processes are described in the context of modular functions (in these example cases, care protocol and resource modules). Note that the modular functions can be executed by the medical device itself, or by a validated companion computing system to which a function was offloaded. Thus, a given modular function may be executed either local to, or remote from, the patient. Data input to a modular function may be derived from data generated local to the patient, and data output by a modular function may be communicated back to the medical device, which in turn uses that data to treat the patient.

Further note that data can be derived from, or converted to, electrical signals. For example, a given functional module may sample or otherwise receive a signal received from a patient sensor of the medical device, and store data descriptive of that signal. The stored data can then be analyzed or otherwise processed by the functional module. As a result of the processing, the functional module can then output data responsive to the input data. The output data can then be translated to an output signal that is communicated back to the medical device. So, in the context of one specific example, an ECG signal from the patient can be received at a functional module (e.g., ECG rhythm analysis module), converted to data, and ventricular fibrillation (V-Fib) can be confirmed through analysis within the module. In response to this determination, the module can generate data responsive to that condition including a shock protocol, and translate that data into output signals that can be transmitted back to the medical device and patient.

Any modules provided herein can exhibit this modular functionality, with signal and/or data inputs and corresponding data and/or signal outputs, as will be appreciated. Thus, this discussion regarding modularity is equally applicable to FIGS. 6 through 9. As will be further appreciated, note that numerous modules may work in conjunction with one another, such that the output of one module is input to another module that then outputs appropriate signals and/or data delivered to the patient (or yet another module). So, for example, an executable care protocol module can be programmed to generate a request (data) for processing by a service component and send that request to an executable resource module. The resource module can be programmed to receive that request and identify a level of service associated with the care protocol module and respond to the request by managing the service component to meet the level of service. To this end, the degree of functional modularity can vary from one embodiment to the next.

Figure 6:
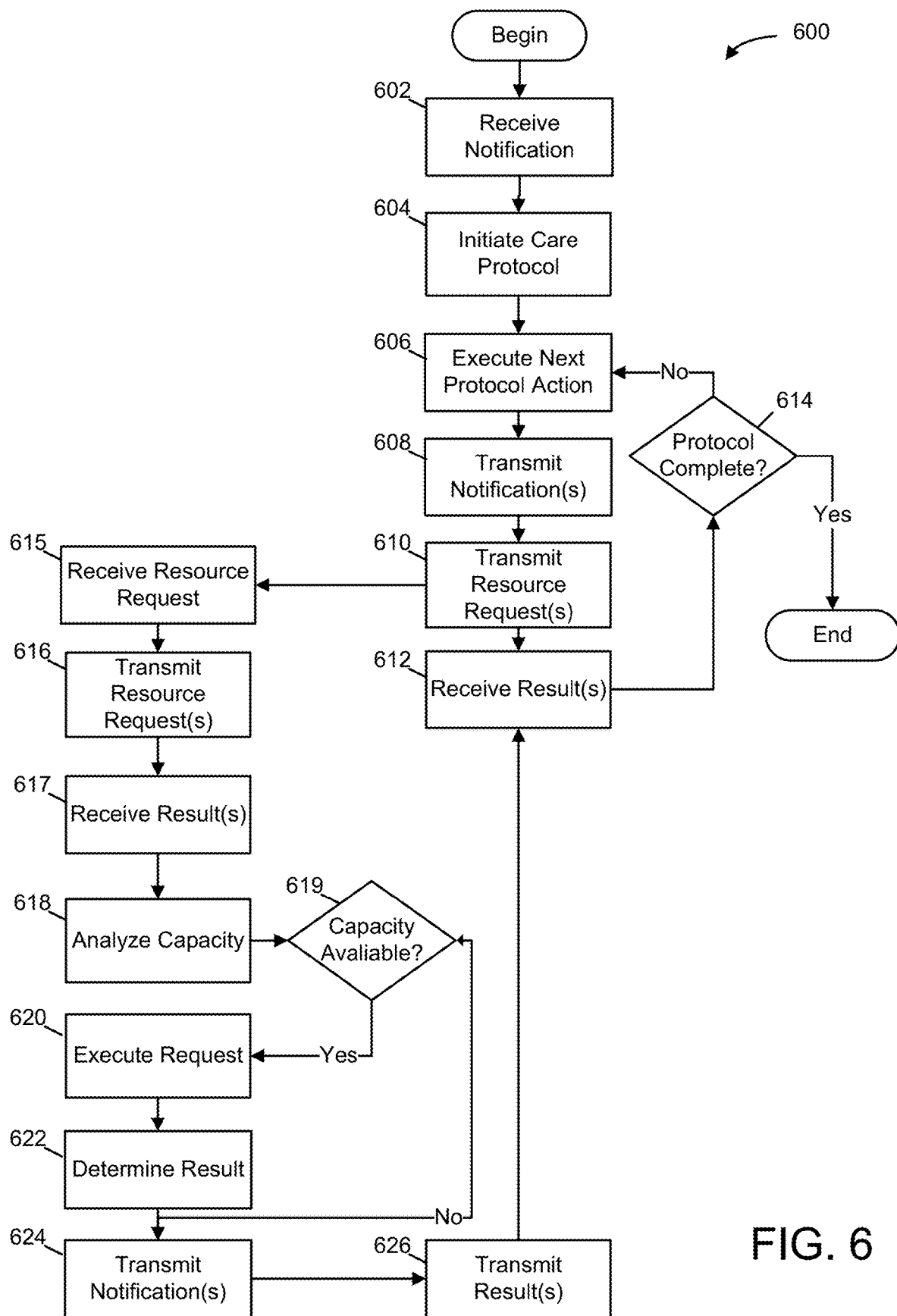
FIG. 6 is a flowchart of example processes executed by care protocol and resource modules, in accordance with an embodiment of the present disclosure.

FIG. 6 is a flowchart of example processes executed by care protocol and resource modules, in accordance with an embodiment of the present disclosure. In act 602, a care protocol module, such as the care protocol module 102 described above with reference to FIG. 1, receives a notification to begin execution. In act 604, the care protocol module initializes execution of a patient care protocol. As described above, in at least one embodiment, within the act 604 the care protocol module determines values of its configuration options and adjusts the patient care protocol to operate in accord with the configuration options.

In act 606, the care protocol module executes the next action specified by the patient care protocol. In act 608, the care protocol module transmits notifications to target components that are registered to receive notifications triggered by execution of the action in the act 606. In act 610, the care protocol module transmits service requests to any resource modules, such as the resource module 108 described above with reference to FIG. 1, managing required service components, such as the common service component 114 described above with reference to FIG. 1.

In act 615, the resource module receives the service request and identifies a level of service and priority associated with the care protocol module. In act 616, the resource module transmits service requests to the other resource modules, if needed. In act 617, the resource module receives results.

In act 618, the resource module determines whether the service component has sufficient capacity to process the service request. In the act 618, the resource module may determine a required allocation of the service component based on the level of service associated with the care protocol module. Where the total capacity of the service component is insufficient to meet the allocation requirement, the resource module determines that sufficient capacity is not available in act 619. Where the total capacity of the service component is sufficient to meet the allocation requirement, the resource module next determines whether the service component has sufficient unallocated capacity to meet the allocation requirement. If so, the resource module determines that sufficient capacity is available in the act 619. Otherwise, the resource module compares a priority associated with the care protocol component to a priority associated with any leaser component(s) to which an amount of the service component's capacity is allocated that when summed with the unallocated capacity is sufficient to meet the allocation requirement. Where the priority associated with the care protocol component is greater than the priority associated with the leaser component(s), the resource module determines that sufficient capacity is available in the act 619. Otherwise, the resource module determines that insufficient capacity is available in the act 619.

In the act 619, the resource module either proceeds to act 620 where sufficient capacity is available or proceeds to the act 624 where insufficient capacity is available. In the act 620, the resource module executes the service request according to its encoded information. In act 622, the resource module determines execution results for the act 620. In the act 624, the resource module transmits notifications to target components that are registered to receive notifications triggered by execution of the action in the act 620. In act 626, the resource module transmits the execution results to the care protocol module.

In act 612, the care protocol module receives the execution results. In act 614, the care protocol module determines whether the patient care protocol is complete. If so, the process 600 ends. Otherwise, the care protocol module executes the next patient care protocol action by return to the act 606.

Processes in accord with the process 600 enable medical devices to execute multiple patient care protocols in a loosely coupled manner, thereby decreasing development and upgrade costs. Moreover, the modular nature of the patient care protocols allows some of them to be offloaded to a companion computing system, if so desired, and when a validated companion system is available.

Example Patient Care Protocols

Figure 7:
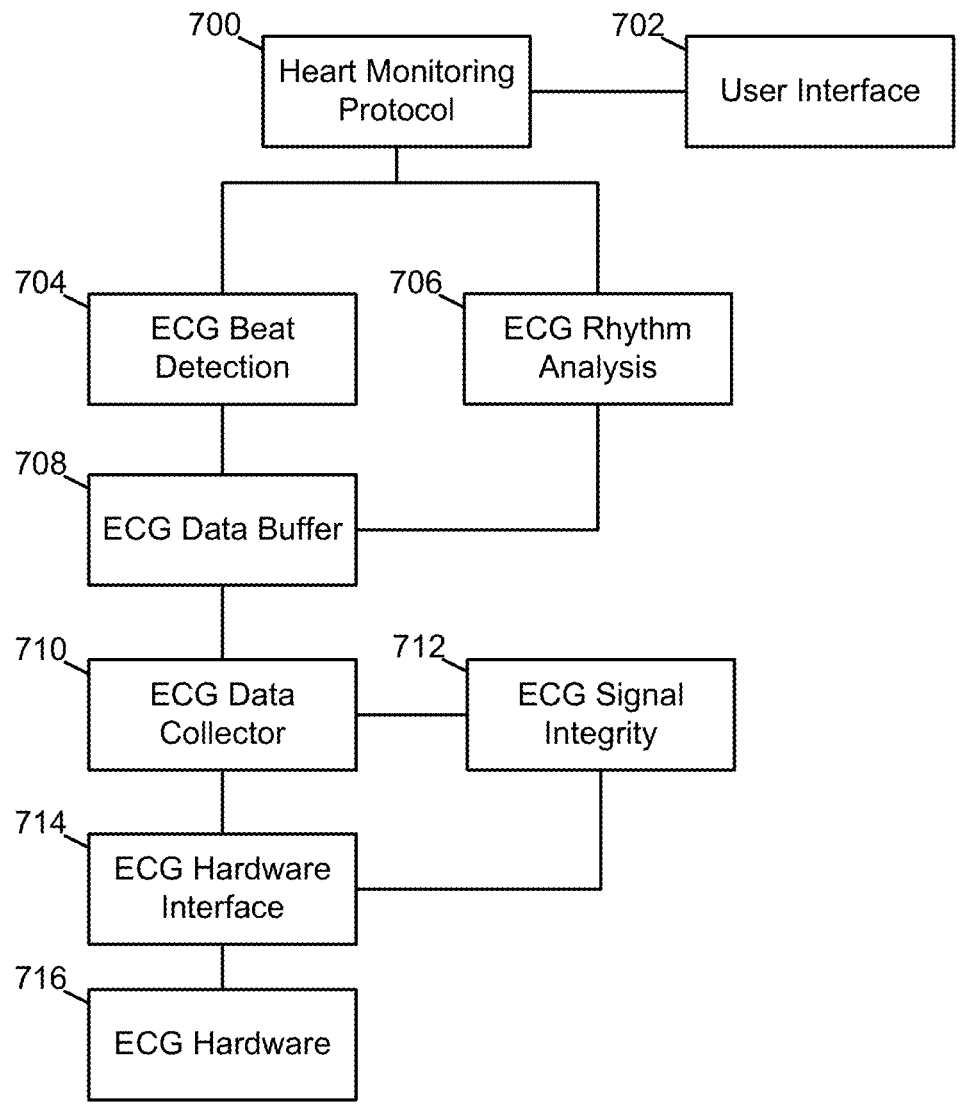
FIG. 7 is a structural diagram of one example of a heart monitoring protocol implemented by care protocol and resource modules, in accordance with an embodiment of the present disclosure.

A variety of patient care protocols may be implemented using the care protocol modules and resource modules described herein, as will be appreciated in light of this disclosure. For instance, FIG. 7 illustrates a structure of care protocol and resource modules configured to implement a heart monitoring protocol. In some embodiments, a medical device executing a heart monitoring protocol analyzes electrical signals produced during cardiac function, monitors integrity of the signals, determines heart rhythm and heart rate from the signals, and addresses any detected abnormal rhythm or rates. The structure illustrated in FIG. 7 includes a heart monitoring care protocol module 700, a user interface resource module 702, an ECG beat detection resource module 704, an ECG rhythm analysis resource module 706, an ECG data buffer resource module 708, an ECG data collector resource module 710, an ECG signal integrity resource module 712, an ECG hardware interface resource module 714, and an ECG hardware 716. Note that any of the modules can be executed locally by the medical device, or offloaded to a local or remote computing system. Thus, data and/or signals input to, and output by, a given module may be passed over a communication network, whether it be a LAN or WAN or combination of both. Note, however, that some or all of the modules may be located in and executed by the medical device controller.

In some embodiments in accord with FIG. 7, the ECG hardware 716 includes analog circuitry configured to gather analog signals produced during cardiac function of a patient. This circuitry may include one or more ECG electrodes. The ECG hardware 716 also includes circuitry (e.g., an analog to digital converter) configured to convert the analog signals to digital signals for further analysis by a processor, such as the processor 218 described above with reference to FIG. 2. Many of components that may be included in the ECG hardware 716 are described above with reference to the sensor interface 212 of FIG. 2 and the medical devices of FIGS. 3-5.

In some embodiments in accord with FIG. 7, the ECG hardware interface resource module 714 is configured to manage the ECG hardware 716. When executing according to this configuration, the ECG hardware interface resource module 714 monitors and controls the ECG hardware 716 and transmits notifications including digital ECG signals and data descriptive of ECG signal integrity to registered components (which may be local to the medical device, or remote from the medical device, as will be appreciated in light of this disclosure). Isolating software interaction with the ECG hardware 716 by executing the ECG hardware interface resource module 714 enables various embodiments disclosed herein to ensure regular, timely processing of ECG related information at an acceptable level of service (e.g., a sampling rate greater than or equal to 250 Hz) that minimizes jitter.

In some example embodiments in accordance with FIG. 7, the ECG signal integrity resource module 712 is configured to receive the data descriptive of ECG signal integrity and analyze the data to determine whether the ECG signal is suitable for further analysis and interpretation. For example, when executing according to this configuration, the ECG signal integrity resource module 712 receives notifications including ECG signal integrity data from the ECG hardware interface 714, receives requests to check ECG signal integrity, determines whether ECG electrodes are properly attached to the patient and whether the ECG signal includes excessive noise, and responds to the requests with information descriptive of the ECG signal integrity.

In some embodiments in accord with FIG. 7, the ECG data collector resource module 710 is configured to receive notifications including ECG data on a periodic basis from the ECG hardware interface resource module 714, receive ECG signal integrity data from the ECG signal integrity resource module 712 in response to requests for the same, determine whether the ECG signal integrity data meets a predefined threshold, and transmit requests for storage of the ECG data and ECG signal integrity data in a buffer managed by the ECG data buffer resource module 708. When executing according to this configuration, the ECG data collector resource module 710 registers to receive ECG data from the ECG hardware interface resource module 714, receives notifications including ECG data from the ECG hardware interface resource module 714, transmits requests to check signal integrity to the ECG signal integrity resource module 712, and transmits requests to the ECG data buffer resource module 708 to store ECG data and ECG signal integrity data.

In some embodiments in accord with FIG. 7, the ECG data buffer resource module 708 is configured to receive data registration requests, requests to store data, and requests to retrieve data. The data and data types encoded within these request may include ECG data samples, ECG signal integrity data, and other status information. In response to receiving these requests, the ECG data buffer resource module 708 processes the requests by accessing a data store, such as the data storage 204 described above with reference to FIG. 2, or some other storage external to the controller 200.

In some embodiments in accord with FIG. 7, the ECG beat detection resource module 704 is configured to analyze ECG data to compute a heart rate of the patient. When executing according to this configuration, the ECG beat detection resource module 704 registers to receive ECG data from the ECG data buffer resource module 708, receives ECG data on a periodic basis from the ECG data buffer resource module 708, computes heart rate data using the received ECG data, transmits notifications including heart rate data to registered components, and transmits requests to store heart rate data to the ECG data buffer resource module 708. In some embodiments in accord with FIG. 7, the ECG beat detection resource module 704 is configured to analyze ECG data to compute a heart rate of the patient. When executing according to this configuration, the ECG beat detection resource module 704 registers to receive ECG data from the ECG data buffer resource module 708, receives ECG data on a periodic basis from the ECG data buffer resource module 708, computes heart rate data using the received ECG data, transmits requests to store heart rate data to the ECG data buffer resource module 708, and transmits notifications including heart rate data to registered components.

In some embodiments in accord with FIG. 7, the ECG rhythm analysis resource module 706 is configured to analyze ECG data to identify the patient's cardiac rhythm. Examples of cardiac rhythms identifiable by the ECG rhythm analysis resource module 706 include normal sinus rhythm, ventricular tachycardia (V-Tach), and ventricular fibrillation (V-Fib). When executing according to its configuration, the ECG rhythm analysis resource module 706 registers to receive ECG data from the ECG data buffer resource module 708, receives ECG data on a periodic basis from the ECG data buffer resource module 708, analyzes the received ECG data to detect cardiac rhythm, transmits requests to store cardiac rhythm data to the ECG data buffer resource module 708, and transmits notifications including cardiac rhythm data to registered components. It will be appreciated that ECG rhythm analysis resource module 706 is capable of supplying data analysis results to multiple source components. For example, where the ECG rhythm analysis resource module 706 receives multiple requests within a time window small enough to not warrant multiple recalculations (e.g., less than 0.8 seconds), the ECG rhythm analysis resource module 706 saves computer resources (e.g., computing cycles) by responding to the requests with a single calculated instance of cardiac rhythm data, rather than responding by recalculating of the same value for each request received.

In some embodiments in accord with FIG. 7, the user interface resource module 702 is configured to manage a user interface, such as the user interface 208 described above with reference to FIG. 2. When executing according to this configuration, the user interface resource module 702 monitors and controls the user interface in response to requests received from the heart monitoring protocol care protocol module 700 (e.g., issuing alarms and processing input received in response to the alarms).

In some embodiments in accord with FIG. 7, the heart monitoring protocol care protocol module 700 is configured to execute a heart monitoring patient care protocol. When executing according to this configuration, the heart monitoring protocol care protocol module 700 registers with the ECG beat detection resource module 704 to receive heart rate data and registers with the ECG rhythm analysis detection resource module 706 to receive cardiac rhythm data. Next, the heart monitoring protocol care protocol module 700 receives heart rate data from the ECG beat detection resource module 704 and receives cardiac rhythm data from the ECG rhythm analysis detection module 706. Next, the heart monitoring protocol care protocol module 700 determines whether the ECG signal integrity is of sufficient quality to support an accurate interpretation (e.g., the ECG signal integrity exceeds a threshold), whether the heart rate data is outside a normal range for the patient, determines whether the rhythm data is abnormal for the patient, and transmits an alarm request to the user interface resource module 702 where the heart rate data is outside the normal range or the rhythm data is abnormal. In one example scenario, each of the heart monitoring protocol care protocol module 700, ECG beat detection resource module 704, and ECG rhythm analysis detection resource module 706 can be offloaded to a companion computing system.

Figure 8:
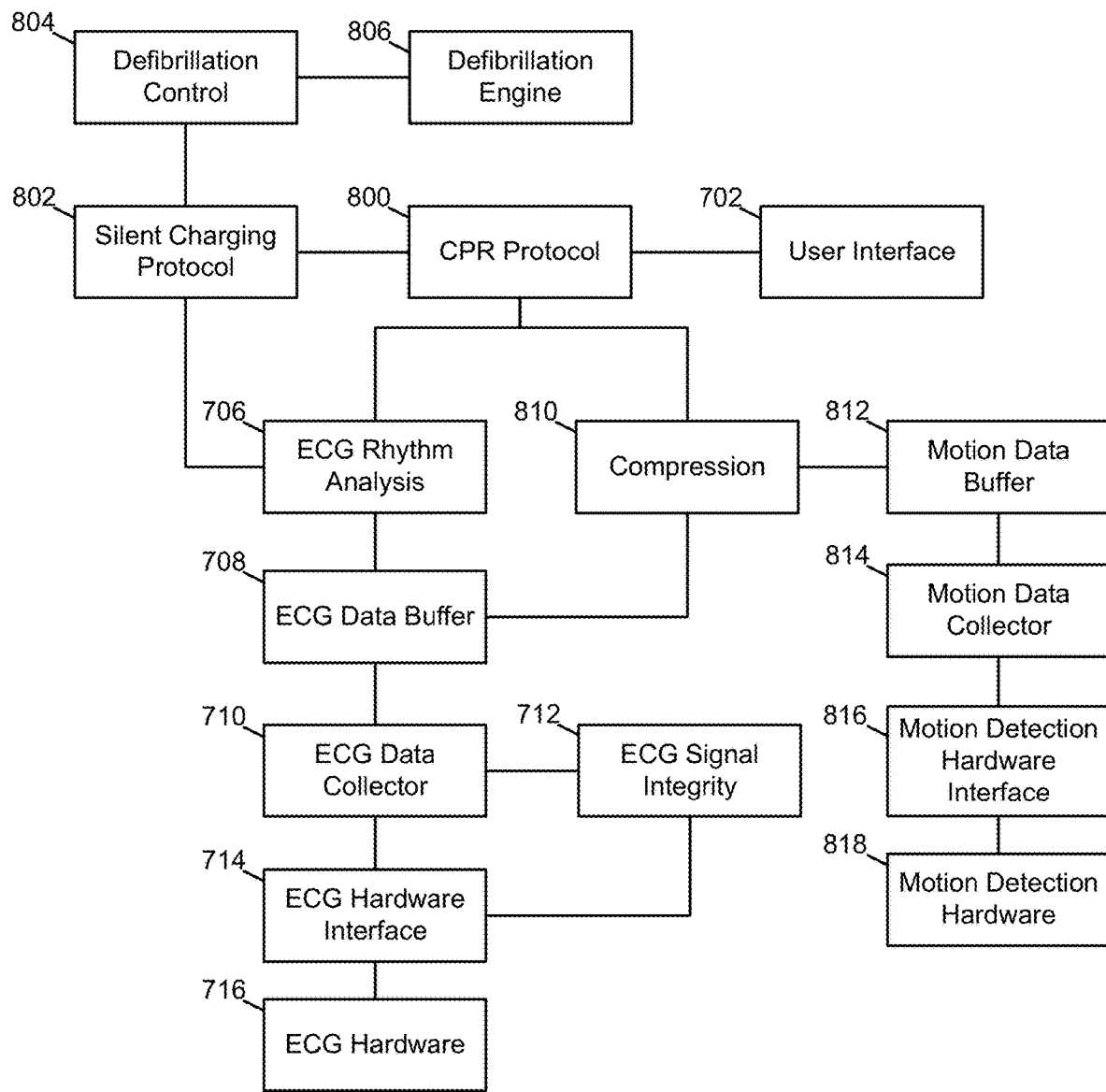
FIG. 8 is a structural diagram of one example of a cardiopulmonary resuscitation (CPR) protocol implemented by care protocol and resource modules, in accordance with an embodiment of the present disclosure.

FIG. 8 illustrates a structure of care protocol and resource modules configured to implement a CPR protocol. Just as explained with respect to FIG. 7, note that any of the modules can be executed locally by the medical device, or offloaded to a local or remote computing system. Thus, data and/or signals input to, and output by, a given module may be passed over some communication network. Other embodiments may be implemented in a stand-alone fashion, as also previously explained.

In some embodiments, a medical device executing the CPR protocol guides a CPR provider through steps required to perform CPR. For instance, the medical device executing the CPR protocol may instruct the CPR provider to administer compressions for a predetermined period of time (e.g., 2 minutes) prior to checking ECG rhythm. In some example CPR protocols, the medical device (or companion computing system or service, as the case may be, if offloaded) instructs the CPR provider to temporarily stop compressions to ventilate the patient via one or more rescue breaths. The structure illustrated in FIG. 8 includes the structure described in FIG. 7 and a CPR protocol care protocol module 800, a silent charging protocol care protocol module 802, a defibrillation resource module 804, a defibrillation engine 806, a compression resource module 810, a motion data buffer resource module 812, a motion data collector resource module 814, a motion hardware interface resource module 816, and motion detection hardware 818.

In some embodiments in accord with FIG. 8, the motion detection hardware 818 includes analog circuitry configured to gather signals produced by patient motion. This circuitry may include one or more accelerometers, gyroscopes, or other motion detectors. The motion detection hardware 818 also includes circuitry (e.g., an analog to digital converter) configured to convert the analog signals to digital signals for further analysis by a processor, such as the processor 218 described above with reference to FIG. 2, or a processor of a companion computing system or remote service. Many of components that may be included in the motion detection hardware 818 are described above with reference to the sensor interface 212 of FIG. 2 and the medical devices of FIG. 3-5. In some embodiments in accord with FIG. 8, the motion detection hardware interface resource module 816 is configured to manage the motion detection hardware 818. When executing according to this configuration, the motion detection hardware interface resource module 816 monitors and controls the motion detection hardware 818 and transmits notifications including digital data descriptive of patient motion to registered components. Again, note that the registered components may be within the medical device itself, or in a companion system or remote service.

In some embodiments in accord with FIG. 8, the motion data collector resource module 814 is configured to register with the motion detection hardware interface 816 to receive notifications including motion data, receive notifications including motion data on a periodic basis from the motion detection hardware interface resource module 816, and transmit requests for storage of the motion data in a buffer managed by the motion data buffer resource module 812. When executing according to this configuration, the motion data collector resource module 814 registers to receive motion data from the motion detection hardware interface resource module 816, receives notifications including motion data from the motion detection hardware interface resource module 816, and transmits requests to the motion data buffer resource module 812 to store motion data. In some embodiments in accord with FIG. 8, the motion data buffer resource module 812 is configured to receive data registration requests, requests to store data, and requests to retrieve data. The data and data types encoded within these request may include motion data samples and other status information. In response to receiving these requests, the motion data buffer resource module 812 processes the requests by accessing a data store, such as the data storage 204 described above with reference to FIG. 2, or some storage facility external to controller 200.

In some embodiments in accord with FIG. 8, the compression resource module 810 is configured to analyze motion data to determine whether chest compressions are being properly performed by the CPR provider. When executing according to this configuration, the compression resource module 810 registers to receive motion data from the motion data buffer resource module 812, receives motion data on a periodic basis from the motion data buffer resource module 812, computes compression depth and rate using the received motion data, transmits notifications including compression depth and rate data to registered components, and transmits requests to store compression depth and rate data to the motion data buffer resource module 812.

In some embodiments in accord with FIG. 8, the CPR protocol care protocol module 800 is configured to guide the CPR provider through performance of CPR. When executing according to this configuration, the CPR protocol care protocol module 800 registers with the compression resource module 810 to receive compression depth and rate data and registers with the ECG rhythm analysis detection resource module 706 to receive cardiac rhythm data. Next, the CPR protocol care protocol module 800 transmits a request to the user interface resource module 702 to display an instruction indicating that compressions should commence and to await a response. Where the instruction is accepted, the CPR protocol care protocol module 800 starts a CPR interval timer. Where the instruction is not accepted within a threshold period of time, the CPR protocol care protocol module 800 discontinues operation. While the CPR interval timer is active (e.g., as a non-zero remaining duration), the CPR protocol care protocol module 800 monitors compression depth and rate data and transmits instructions to the CPR provider to adjust compression depth and rate as needed for proper performance of CPR. When the CPR interval timer expires, the CPR protocol care protocol module 800 transmits a request to the user interface resource module 702 to display an instruction indicating that the patient's pulse should be checked and restarts the CPR interval timer. Next, the CPR protocol care protocol module 800 requests and receives cardiac rhythm data from the ECG rhythm analysis detection module 706. While the CPR interval timer remains active, the CPR protocol care protocol module 800 determines whether the cardiac rhythm data indicates that the patient is experiencing a cardiac arrhythmia (e.g., VT or VF). If the CPR protocol care protocol module 800 determines that the patient is experiencing an arrhythmia, the CPR protocol care protocol module 800 transmits a request to the user interface resource module 702 to display a message indicating that the patient is experiencing an arrhythmia. If the patient continues to experience the arrhythmia when the remaining duration of the CPR interval timer reaches a predefined threshold (e.g., 10 seconds), the CPR protocol care protocol module 800 transmits a request initiate charging to the silent charging protocol care protocol module 802.

In some embodiments in accord with FIG. 8, the silent charging protocol care protocol module 802 is configured to ready a defibrillator for delivery of a therapeutic shock to the patient. When executing according to this configuration, the silent charging protocol care protocol module 802 registers with the ECG rhythm analysis detection resource module 706 to receive cardiac rhythm data and registers with the defibrillation control resource module 804 to receive defibrillation status notifications. Next, the silent charging protocol care protocol module 802 waits for requests from other components. Responsive to receiving a request to initiate charging, the silent charging protocol care protocol module 802 determines whether automatic charging is enabled by inspecting the value of a configuration option. If automatic charging is enabled, the silent charging protocol care protocol module 802 next determines whether the patient is experiencing a treatable arrhythmia (e.g., V-Tach or V-Fib). If the silent charging protocol care protocol module 802 determines that the patient is experiencing a treatable arrhythmia, the silent charging protocol transmits a request to the defibrillation control resource module 804 to initiate silent charging. If automatic charging is not enabled, the silent charging protocol care protocol module 802 responds to the request to initiate charging with an indication that automatic charging is not available. Responsive to receiving a transmission from the defibrillation control resource module 804, the silent charging protocol care protocol module 802 determines the type of transmission received. Where the type of transmission is a notification regarding charge progress (other than a notification that the charge process is complete), the silent charging protocol care protocol module 802 acknowledges the transmission, but does not interact with the user interface 702, as the silent charging protocol care protocol module 802 is not designed to communicate with the patient or the CPR provider. Where the type of transmission is a notification that the charge process is complete, the silent charging protocol care protocol module 802 responds to the request to initiate charging with information indicating charging is complete.

In some embodiments in accord with FIG. 8, the defibrillation control resource module 804 is configured to manage charging of a defibrillation subsystem in preparation for discharge of a therapeutic shock. Management of the defibrillation subsystem by a single resource control module ensures exclusive control of the defibrillation subsystem by a single care protocol module. When executing according to this configuration, the defibrillation control resource module 804 may receive a request to charge the defibrillation hardware from the silent charging protocol care protocol module 802. Responsive to receiving a request to charge, the defibrillation control resource module 804 transmits a status request to the defibrillation engine 806 to determine whether the defibrillation engine is idle. If the defibrillation control resource module 804 determines that the defibrillation engine 806 is idle, the defibrillation control resource module 804 transmits a request to start charging to the defibrillation engine. If the defibrillation control resource module 804 determines that the defibrillation engine 806 is already active, the defibrillation control resource module 804 responds to the request to charge with information indicating that silent charging is not available.

In some embodiments, the defibrillation control resource module 804 may also receive a request to switch to a monitor only mode of operation. In response to receiving such a request, the defibrillation control resource module 804 transmits a request to the defibrillation engine 806 to stop charging.

In some embodiments, the defibrillation control resource module 804 may also receive a request to adjust energy delivered in future therapeutic shocks. In response to receiving such a request, the defibrillation control resource module 804 transmits a request to the defibrillation engine 806 to adjust its charging energy.

In some embodiments, the defibrillation control resource module 804 may also receive a request to provide information regarding charge progress. In response to receiving such a request, the defibrillation control resource module 804 transmits a request to the defibrillation engine 806 to respond with its charge status. Responsive to receiving the charge status, the defibrillation control resource module transmits information descriptive of the current charge status to the component requesting the charge status.

In some embodiments, the defibrillation control resource module 804 may also receive a transmission from the defibrillation engine indicating that the defibrillation hardware is completely charged. In response to receiving such a transmission, the defibrillation control resource module 804 transmits a notification indicating the charge is complete to the silent charging protocol care protocol module 802.

In some embodiments in accord with FIG. 8, the defibrillation engine 806 includes hardware and software components used to prepare and delivery a therapeutic shock to the patient. These components may include, for example, the battery 210, the processor 218, and the therapy delivery interface 202 described above with reference to FIG. 2. Other components of the defibrillation engine are described with reference to the example medical devices of FIGS. 3-5. An example offloading scheme according to one possible scenario might be, for instance, where the CPR protocol care protocol module 800 and compression resource module 810 are offloaded to a companion computing system or remote service.

Figure 9:
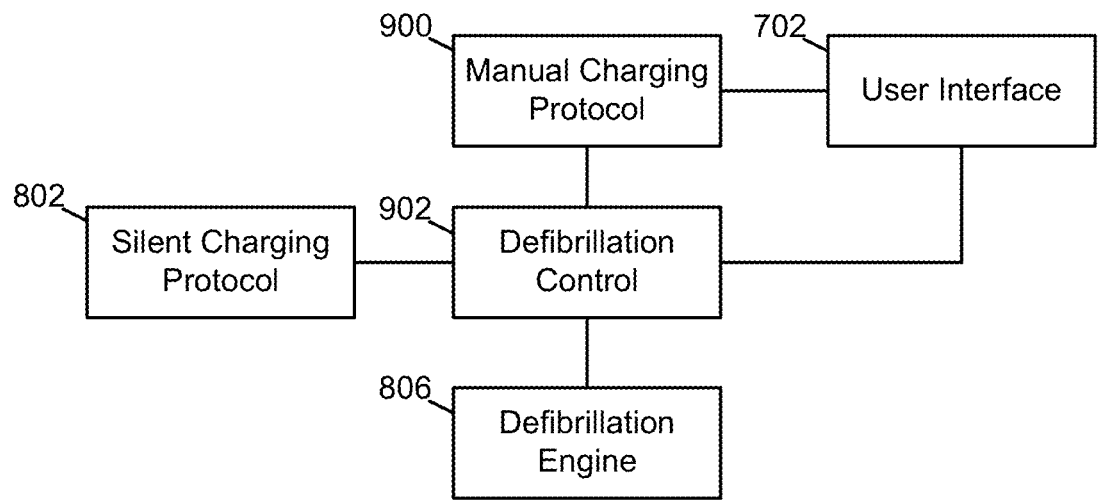
FIG. 9 is a structural diagram of one example of components used to manage defibrillation hardware within a medical device, in accordance with an embodiment of the present disclosure.

FIG. 9 illustrates a structure of care protocol and resource modules in which contention for the defibrillation engine 806 may occur between a manual charging protocol care protocol module 900 and the silent charging protocol care protocol module 802. The structure illustrated in FIG. 9 includes the manual charging protocol care protocol module 900, the defibrillation control resource module 902, the user interface resource module 702 described above with reference to FIG. 7, and the silent charging protocol care protocol module 802 and the defibrillation engine 806 described above with reference to FIG. 8. Just as explained with respect to FIGS. 7 and 8, note that any of the modules can be executed locally by the medical device, or offloaded to a local or remote computing system. Thus, data and/or signals input to, and output by, a given module may be passed over some communication network. Other embodiments may be implemented in a stand-alone fashion, as also previously explained.

In some embodiments in accord with FIG. 9, the manual charging protocol care protocol module 900 is configured to enable a CPR provider to manually charge the defibrillation subsystem of the medical device in preparation for discharge of a therapeutic shock. When executing according to this configuration, the manual charging protocol care protocol module 900 registers to receive status notifications from the defibrillation control resource module 804 and the user interface 702. In response to receiving a notification of input selecting a manual charge button of the user interface, the manual charging protocol care protocol module 900 transmits a request to the defibrillation control resource module 804 to initiate audible charging. Where the manual charging protocol care protocol module 900 receives a notification of charge progress from the defibrillation control resource module 804, the manual charging protocol care protocol module 900 transmits a request to the user interface resource module to update the user interface with the charge progress. Where the manual charging protocol care protocol module 900 receives a notification of charge completeness from the defibrillation control resource module 804, the manual charging protocol care protocol module 900 transmits a request to the user interface resource module to update the user interface with the charge progress and illuminate a shock button. Where the manual charging protocol care protocol module 900 receives a notification of charge cancellation from the defibrillation control resource module 804, the manual charging protocol care protocol module 900 transmits a request to the user interface resource module to update the user interface with a message indicating that defibrillation subsystem charging has been canceled.

In some embodiments in accord with FIG. 9, the defibrillation control resource module 902 is configured to manage charging of a defibrillation subsystem in preparation for discharge of a therapeutic shock. Management of the defibrillation subsystem by a single resource control module ensures exclusive control of the defibrillation subsystem by a single care protocol module. When executing according to this configuration, the defibrillation control resource module 902 may receive transmissions from the silent charging protocol care protocol module 802 and the manual charging protocol care protocol module 900. Responsive to receiving a request to charge, the defibrillation control resource module 902 transmits a status request to the defibrillation engine 806 to determine whether the defibrillation engine is idle. If the defibrillation control resource module 902 determines that the defibrillation engine 806 is idle, the defibrillation control resource module 902 transmits a request to start charging (either silent charging or audible charging, as received from either the silent charging protocol care protocol module 802 or the manual charging protocol care protocol module 900) to the defibrillation engine. If the defibrillation control resource module 902 determines that the defibrillation engine 806 is already active, the defibrillation control resource module 902 responds to the request to charge with information indicating that charging is not currently available.

In some embodiments, the defibrillation control resource module 902 may also receive a request to switch to a monitor only mode of operation. In response to receiving such a request, the defibrillation control resource module 902 transmits a request to the defibrillation engine 806 to stop charging.

In some embodiments, the defibrillation control resource module 902 may also receive a request to adjust energy delivered in future therapeutic shocks. In response to receiving such a request, the defibrillation control resource module 902 transmits a request to the defibrillation engine 806 to adjust its charging energy.

In some embodiments, the defibrillation control resource module 902 may also receive a request to provide information regarding charge progress. In response to receiving such a request, the defibrillation control resource module 902 transmits a request to the defibrillation engine 806 to respond with its charge status. Responsive to receiving the charge status, the defibrillation control resource module transmits information descriptive of the current charge status to the component requesting the charge status.

In some embodiments, the defibrillation control resource module 902 may also receive a transmission from the defibrillation engine indicating that the defibrillation hardware is completely charged. In response to receiving such a transmission, the defibrillation control resource module 902 transmits a notification indicating the charge is complete to the silent charging protocol care protocol module 802 or the manual charging protocol care protocol module 900, whichever is the active charging protocol.

Figure 11:
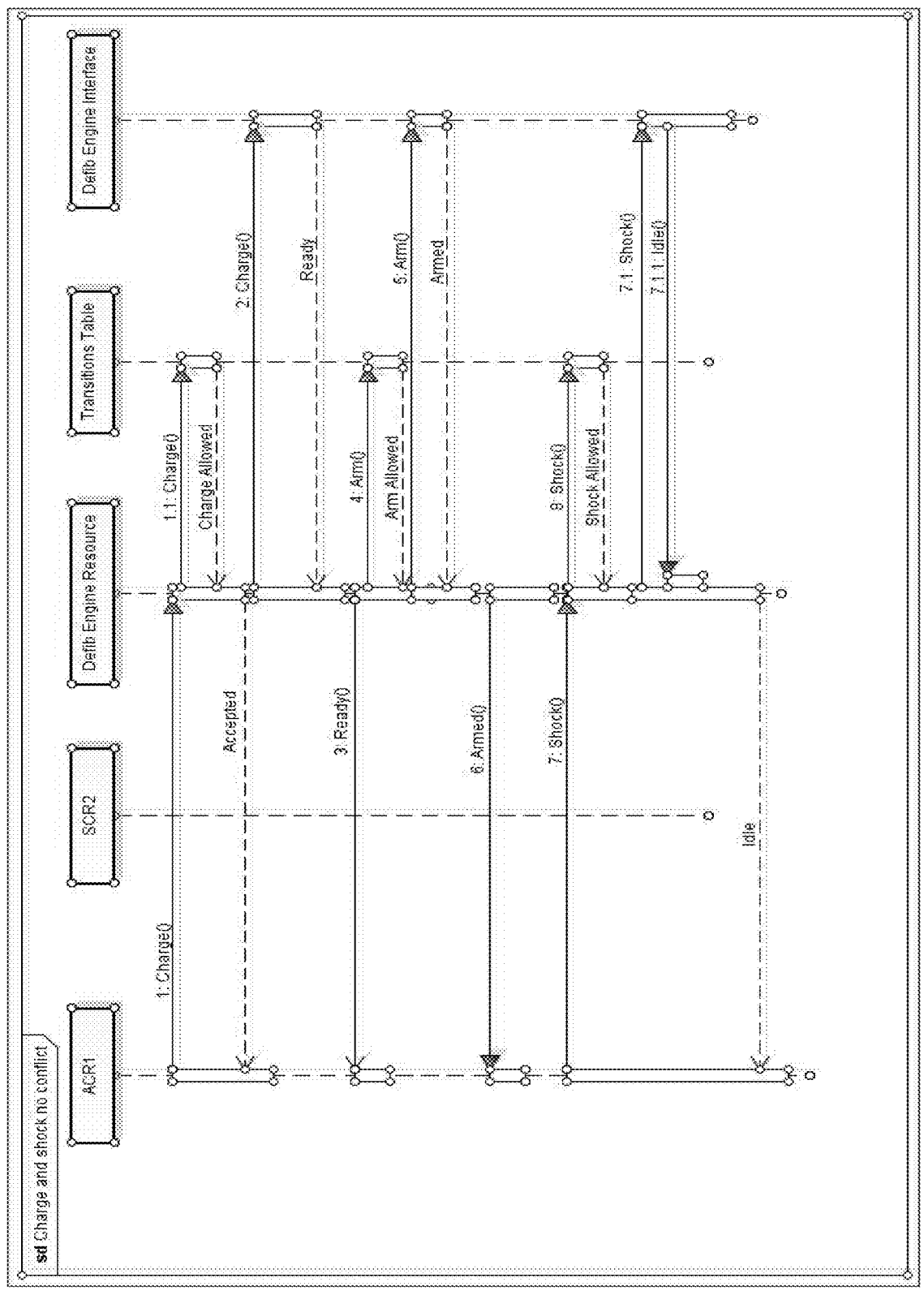
FIG. 11 is sequence diagram depicting a sequence of interactions, in accordance with an embodiment of the present disclosure.

FIG. 11 illustrates component interactions executed by a medical device that includes a conflict arbitration engine, such as the conflict arbitration engine 1002 described above with reference to FIG. 10. As shown in FIG. 11, audible charge component (ACR1) transmits a request to a defibrillation engine resource module to charge the defibrillator. In this example, ACR1 has the highest priority and the defibrillation engine resource module is Idle. In response to receiving the request, the defibrillation engine resource module identifies that the current state of the defibrillation engine resource module is idle (which indicates that the defibrillator capacitor is idle), determines that the transition from idle to charge is valid, and, in response to these actions, invokes the charge( ) function to charge the defibrillator capacitor. The defibrillation engine resource module may determine that the transition is valid by referencing a conflict resolution table, such as Table 2 described below. Next, the defibrillation engine resource module transmits a notification to ACR1 that indicates ACR1's request has been accepted and that the defibrillator is charging. When charging finishes, the defibrillation engine resource module transmits a notification to ACR1 that indicates the defibrillation engine resource module has transitioned to ready state.

Next, in the example embodiment illustrated in FIG. 11, ACR1 transmits a request to arm to the defibrillation engine resource module. In response to receiving the request, the defibrillation engine resource module identifies that the current state of the defibrillation engine resource module is ready, determines that the transition from ready to armed is valid, and, in response to these actions, invokes the arm( ) function. The arm( ) function illuminates a shock button of the medical device. In addition, the defibrillation engine resource module transmits a notification to ACR1 that indicates the defibrillation engine resource module has transitioned to an armed state.

Next, in the example embodiment illustrated in FIG. 11, ACR1 transmits a request to shock to the defibrillation engine resource module. In response to receiving the request, the defibrillation engine resource module identifies that the current state of the defibrillation engine resource module is armed, determines that the transition from armed to shock is valid, and, in response to these actions, invokes the shock( ) function. The shock( ) function causes the medical device to deliver of a therapeutic shock. After execution of the shock( ) function, the defibrillation engine resource module detects that the defibrillator capacitor is idle and, in response, transmits a notification to ACR1 that indicates the defibrillation engine resource module has transitioned to an idle state. In this example, the medical device is configured such that the only state transition that allows a shock to be delivered is armed to shock transition. A shock request may be initiated when the shock button is pushed or when requested by an AED protocol implementation.

Figure 12:
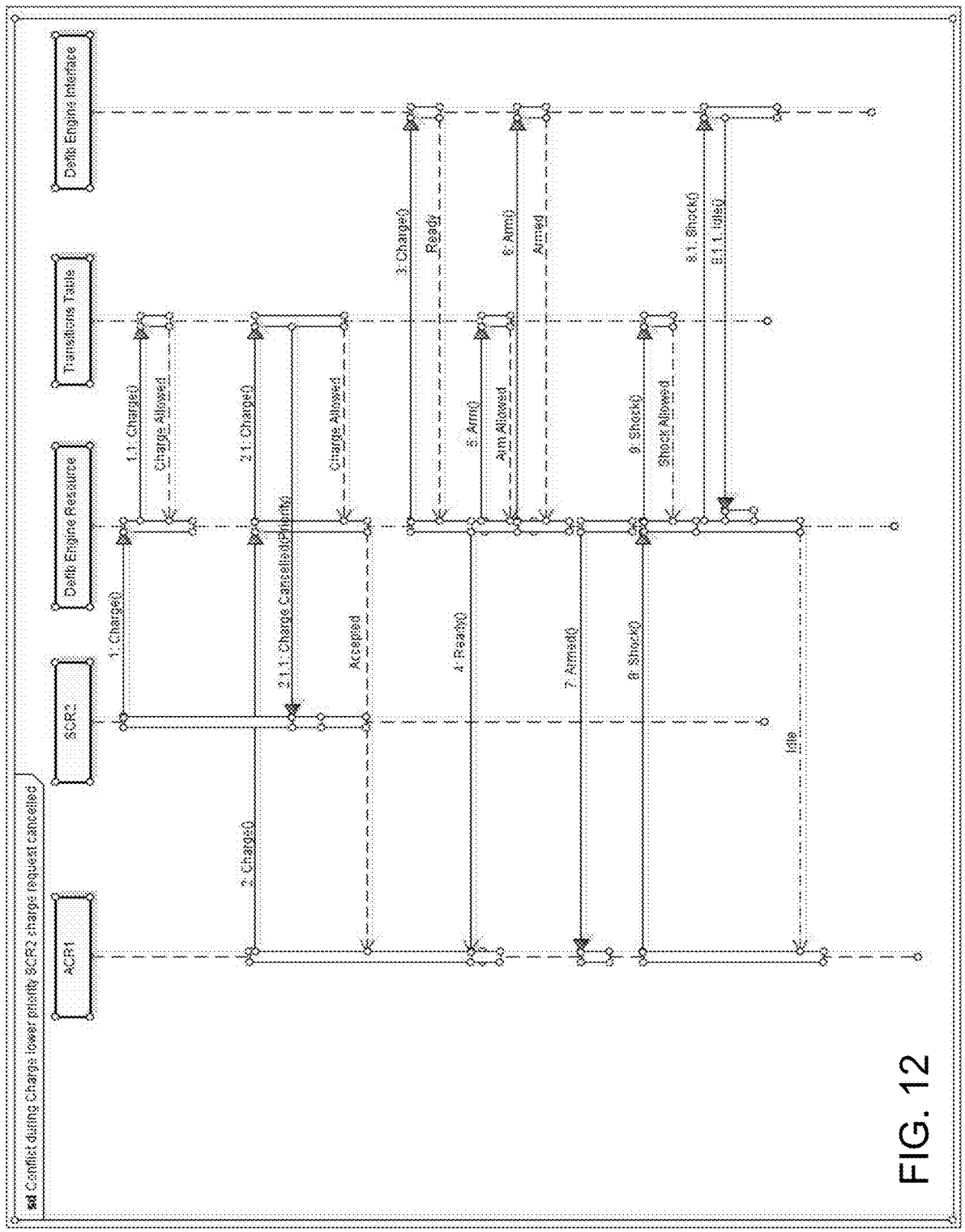
FIG. 12 is sequence diagram depicting a sequence of interactions, in accordance with another embodiment of the present disclosure.

FIG. 12 illustrates component interactions executed by a medical device that includes a conflict arbitration engine, such as the conflict arbitration engine 1002 described above with reference to FIG. 10. As shown in FIG. 12, a silent charge component (SCR2) transmits a request to a defibrillation engine resource module to charge the defibrillator. In this example, SCR2 has a lower priority than the audible charge component (ACR1) and the defibrillation engine resource module is Idle. In response to receiving the request, the defibrillation engine resource module identifies that the current state of the defibrillation engine resource module is idle (which indicates that the defibrillator capacitor is idle), determines that the transition from idle to charge is valid, and, in response to these actions, invokes the charge( ) function to charge the defibrillator capacitor. Next, the defibrillation engine resource module transmits a notification to SCR2 that indicates SCR2's request has been accepted and that the defibrillator is charging.

Next ACR1 transmits a request to a defibrillation engine resource module to charge the defibrillator. The defibrillation engine resource module identifies its current state as charging and thereby detects a conflict between two requests. The defibrillation engine resource module transmits an arbitration request to the conflict arbitration engine. The conflict arbitration engine identifies the requests in a priority table (e.g., Table 3 below) and determines that ACR1's request has higher priority than SCR2's request. In response to making this determination, the conflict arbitration engine cancels SCR2's request and transmits a response to the defibrillation engine resource module indicating that SCR2's request has been canceled due to a higher priority request. In response to receiving this notification, the defibrillation engine resource module transmits a notification indicating the cancelation to SCR2 and transmits a notification to ACR1 indicating that its request has been accepted and that the defibrillator capacitor is charging. When charging finishes, the defibrillation engine resource module transmits a notification to ACR1 that indicates the defibrillation engine resource module has transitioned to ready state.

Next, in the example embodiment illustrated in FIG. 12, ACR1 transmits a request to arm to the defibrillation engine resource module. In response to receiving the request, the defibrillation engine resource module identifies that the current state of the defibrillation engine resource module is ready, determines that the transition from ready to armed is valid, and, in response to these actions, invokes the arm( ) function. The arm( ) function illuminates a shock button of the medical device. In addition, the defibrillation engine resource module transmits a notification to ACR1 that indicates the defibrillation engine resource module has transitioned to an armed state.

Next, in the example embodiment illustrated in FIG. 12, ACR1 transmits a request to shock to the defibrillation engine resource module. In response to receiving the request, the defibrillation engine resource module identifies that the current state of the defibrillation engine resource module is armed, determines that the transition from armed to shock is valid, and, in response to these actions, invokes the shock( ) function. The shock( ) function causes the medical device to deliver of a therapeutic shock. After execution of the shock( ) function, the defibrillation engine resource module detects that the defibrillator capacitor is idle and, in response, transmits a notification to ACR1 that indicates the defibrillation engine resource module has transitioned to an idle state. In this example, the medical device is configured such that the only state transition that allows a shock to be delivered is armed to shock transition. A shock request may be initiated when the shock button is pushed or when requested by an AED protocol implementation.

Table 2 of FIG. 13A illustrates one example of a populated conflict resolution table that may be referenced during the operations and interactions described above with reference to FIGS. 11 and 12. Table 3 of FIG. 13B illustrates one example of a populated source component priority table that may be referenced during the operations and interactions described above with reference to FIG. 12.

Offloading of Modular Functions

FIG. 14A illustrates a methodology for offloading modular functions from a medical device to a companion computing system, in accordance with an embodiment of the present disclosure. The methodology may be carried out, for example, by the offload module 224 of the medical device controller 200; however, the functionality can be integrated into any number of systems, as will be appreciated. As can be seen, the medical device may operate in stand-alone fashion, if offloading is not available, for whatever reason. However, if the medical device detects the presence of companion computing system and verifies the authenticity of the system, the medical device many then assign or otherwise offload some of its modular functions to that system. The companion computing system may be, for example, a mobile computing device (e.g., tablet, or smartphone, or more advanced medical device having greater functionality than the initial medical device) or remote or so-called cloud-based service accessible by the Internet or other WAN.

The method includes determining 1401 if a communication network (e.g., wired or wireless LAN, etc) is available. If not, the method includes continuing 1403 with stand-alone operation of the medical device (no offloading). On the other hand, if a network is detected at 1401, the method continues with discovering 1405 one or more potential companion systems on the network and executing an authentication process. The method continues with determining 1407 if a given companion computing system authenticates correctly. If not, the method includes continuing 1403 with stand-alone operation of the medical device (no offloading).

On the other hand, if a given companion computing system is determined to be authentic at 1407, the method continues with identifying 1409 one or more modular functions approved for offloading. As will be further appreciated, the modular functionality that can be offloaded may vary from one embodiment to the next. In other example cases, the modular functionality approved for offloading includes: display function, video recording function, audio recording function, and various rescue functions such as ECG rhythm analysis, compression analysis, CPR timing, user prompting, manual charge/shock capability (for medical professionals), and any other modular functions. In a more general sense, hardware-based functions that generate real-time patient data used to assess and treat a given patient can remain in the medical device, and any control functions that analyze the collected patient data and issue corresponding treatment commands, prompts and other rescue protocols can be offloaded to the companion computing system.

In some embodiments, the modular functions approved for offloading are pre-established and stored in a memory. In such cases, the identifying at 1409 can be accomplished by consulting the memory. In other embodiments, the modular functions approved for offloading may be more dynamic in nature, and depend on factors of the given situation. For instance, if a display and video capabilities of the authenticated companion system are recorded as being better than those capabilities of the medical device, then the display and video functions can be approved for offloading. In a similar fashion, if the authenticated companion system is recorded as being an advanced version of the medical device or an otherwise advanced supplementary component capable of supporting the medical device, then control functions and rescue protocols can be approved for offloading. In still other embodiments, demand on computing resources of the medical device that exceeds a given threshold can provide the basis for offloading certain modular functions. For instance, image analysis of a video showing CPR being carried out on the patient can be computationally intensive, and such image analysis can thus be offloaded to the companion system.

Numerous other such offloading use cases will be apparent in light of this disclosure. Table 4 below shows another example embodiment, where functions related to capturing patient data (e.g., ECG signals, CPR signals, patent impedance to ensure electrodes are attached properly, cable type, and user inputs) are carried out by the medical device and not offloaded, and functions related to commands and prompts based on that patient data are offloaded to the companion system.

TABLE 4

Example modular functions offloaded to companion system

| Medical Device | Companion System |
|---|---|
| ECG Signals (e.g., 250 Hz) | |
| CPR Signals (e.g., 125 Hz) | |
| Patient Impedance (e.g., 10 Hz) | |
| Cable Type (e.g., 10 Hz) | |
| | Defibrillator Commands (e.g., charge, shock, dump) |
| | Prompts (e.g., text, audio, shock enabled) |
| User Inputs (e.g., shock button pressed) | |

Once a companion system is engaged and validated, and the modules approved for offloading are identified or otherwise determined, the method continues with offloading 1411 the approved modular functions to the companion system, and determining 1413 whether offload was successful. If not, the method includes continuing 1403 with stand-alone operation of the medical device (no offloading). One or more re-tries may be allowed, if appropriate given the circumstances. To this end, note that patient safety and health can be readily prioritized higher than such re-tries or other secondary processing efforts. On the other hand, if the offload was successful, the method may continue with monitoring 1415 the communication link. This monitoring may be carried out continuously to ensure a robust communication link). If the communication link fails, then the method includes transitioning back to stand-alone operation of the medical device (no offloading), at 1403; otherwise, the medical device and companion system continue to collectively operate in effort to mitigate treatable conditions of the patient. The offloaded arrangement will continue until terminated by some event (e.g., lost communication link thereby causing return to stand-alone operation, treatment is completed, manual termination by user, etc).

The offloading process at 1411 can be carried out in a number of ways. In some example embodiments, the offloaded modules are pre-installed into a memory of the companion system by virtue of those modules being part of a companion application executing on the companion system. In such cases, the offloaded modules can begin execution once offloading has been signaled. Note that detecting the companion application installed on the companion system can be part of the authentication process. Further note that if the application is out of date, the methodology may be further programmed or otherwise configured to command/request the companion system to perform an application upgrade, and postpone any offloading until that upgrade is confirmed as being completed by the companion system. In other embodiments, executable versions of the modules approved for offloading can be forwarded from the medical device to the companion system via the network. In such cases, an application executing on the companion device can be configured to receive those modules and initiate execution of same. Further note that any number of mechanisms can be used to synchronize the start and end of execution of a given offloaded module. For instance, a bit can be set in the real-time data stream that includes the patient data.

Further note that the various functionalities associated with the offloaded modules can be turned off or otherwise suppressed at the medical device, until that medical device is returned to stand-alone operation, as will be appreciated. This can be accomplished, for instance, by setting a flag or bit in the data 122 or instructions 120 or interface 118 of a care protocol module located in the medical device corresponding to the offloaded function. Likewise, a flag or bit can be set in the data 128 or instructions 126 or interface 124 of a resource module located in the medical device corresponding to the offloaded function. All such flags can be reset, for instance, when a call to return to stand-alone mode is received, or when an offloaded function is terminated for whatever reason. A failsafe arrangement can be used to ensure that the modular function is either identified to be executing on the companion system, or otherwise defaults to executing on the medical device if execution on the companion system cannot be confirmed, in some embodiments.

The determination at 1413 as to whether the offload was successful can be carried out in a number of ways. In some cases, for instance, in response to receiving predefined test data from the medical device, the offloaded module is programmed to transmit an acknowledgement back to the source module of the medical device to confirm the offload process is successfully executing. Numerous other handshake or acknowledgement schemes can be used, as will be appreciated.

FIG. 14B illustrates a system for offloading select modular functions from a medical device to a companion computing system, in accordance with an embodiment of the present disclosure. As can be seen, the medical device with the controller 200 is communicatively coupled with a companion computing system 1450 via a local wireless network, and has offloaded one or more modular functions to that system 1450. Patient data and/or queries are provided from the medical device to the companion system 1450, and appropriate responses are provided from the companion system 1450 to the medical device. The patient data may include, for instance, real-time ECG, CPR acceleration, patient impedance (indication if electrodes are attached properly), and cable data (indication that cables provide a continuous circuit, rather than an open circuit). The response may be, for instance, a rescue protocol suitable for the patient's condition, such as CPR instructions ("begin chest compression", followed by audible beat for compression timing), shock-related instructions (e.g., "do not touch patient"), and control signals (e.g., delivery of shock to patient).

The offloaded modules may be, for instance, a heart monitoring protocol care protocol module 700, ECG beat detection resource module 704, an ECG rhythm analysis detection resource module 706, a CPR protocol care protocol module 800, a compression resource module 810, a silent charging protocol care protocol module 802, and a defibrillation control resource module 804. As previously explained, non-medical related functions may be offloaded as well, such as a display function and/or an audio function. For instance, in the example embodiment shown in FIG. 14B, the companion system 1450 optionally outputs instructive visual and audio data to a display and a speaker. In addition, the companion system 1450 may execute a video function so as to capture video of the patient and treatment regimen, and stream that video to some remote healthcare provider service via a WAN (e.g., Internet). Note that the video function may not actually be an offloaded function (e.g., in some cases, the medical device simply doesn't have video capability, but the companion system does, thereby providing another benefit or reason for the communicative coupling between the medical device and the companion system 1450.

The companion system 1450 can be any number of computing systems, such as a laptop, tablet, smartphone, or advanced medical system. In any such cases, the companion system 1450 can be loaded with an application programmed to seek out communications from the medical device, so as to facilitate the discovery and authentication process. In one example scenario, the companion system 1450 is a more advanced or otherwise more comprehensive medical system (relative to the medical device with controller 200). In some such cases, the medical device with controller 200 can determine the presence of the more advanced medical system 1450 (e.g., during the discovery process at 1405), and offload or otherwise yield all or select local control functions to the more advanced medical system 1450 under certain conditions.

In some example cases, note that the medical device with controller 200 may be, for example, a field AED that is worn by the patient or deployed on the premises where the patient experienced a cardiac episode. In any case, the field AED provides a base level of care suitable for stand-alone operation. The medical system 1450 may be configured to provide advanced support to that field AED. The medical system 1450 may be, for instance, deployed by paramedics arriving on scene. Such an intentional device-system pairing can be used to provide a higher level of care and facilitate rapid establishment of communication between the field device and the paramedic system 1450 for a robust chain of resuscitation. Moreover, note that the lower complexity of the field device allows for proliferation of base level treatment options that can be further supplemented with advanced technology upon arrival of medical professionals trained to exploit that advanced technology.

FIG. 14C illustrates a system for offloading select modular functions from a medical device to a companion computing system or service, in accordance with another embodiment of the present disclosure. As can be seen, the medical device with controller 200 at a rescue site is communicatively coupled with a remote companion system via a LAN/WAN arrangement (e.g., local Wi-Fi connective to the Internet, campus network, etc). In this example case, the remote companion system is a remote medical provider service. As will be appreciated, one or more modular functions can be offloaded from the medical device to the service, just as explained with respect to the embodiment of FIG. 14B, except that the communication path through the network may be longer. In any case, the previous relevant discussion may equally be applied here, in some embodiments.

In the example scenario depicted, the local medical device with controller 200 is streaming patient data to the service. The service receives and analyzes the patient data, and streams back audio prompts and directions to the patient site to assist in the care of the patient. The patient data may include, for instance, real-time ECG, CPR acceleration, patient impedance, and cable data, and streaming video. The response may be, for instance, a rescue protocol suitable for the patient's condition, such as CPR instructions ("begin chest compression", followed by audible beat for compression timing), shock-related instructions (e.g., "do not touch patient"), and control signals (e.g., delivery of shock to patient). Also, given that the service can visually monitor delivery of CPR, the service may give further verbal instruction (e.g., "you are too low on the chest, move your hands up two inches"). As can be further seen, the service monitors the live feed of CPR data from the rescue site.

FURTHER EXAMPLE EMBODIMENTS

The following examples pertain to further embodiments, from which numerous permutations and configurations will be apparent.

Example 1 is a medical device comprising: a service component for use in detecting patient data; at least one processor; a care protocol module executable by the at least one processor to provide healthcare to a patient at least in part by generating a request for processing by the service component; and a resource module executable by the at least one processor to manage access to the service component by identifying a level of service associated with the care protocol module and responding to the request by managing the service component to meet the level of service. The care protocol module implements a patient care protocol that includes a sequence of actions directed to the patient that can be repeated, terminated, or altered dynamically; and the level of service indicates a level of performance that the patient care protocol requires of the resource module.

Example 2 includes the subject matter of Example 1, wherein there are at least two care protocol modules, each configured to generate a request for processing by the service component, and the medical device further comprises: a conflict arbitration engine configured to resolve conflicts between multiple requests for processing by the service component at least in part by comparing the multiple requests, identifying a source component associated with at least one request of the multiple requests, and initiating processing of the at least one request.

Example 3 includes the subject matter of Example 1 or 2, wherein the resource module is executable by the at least one processor to respond to the request at least in part by translating the level of service into an allocation requirement for a capacity of the service component, and managing the service component includes allocating the capacity of the service component to the request according to the allocation requirement.

Example 4 includes the subject matter of any of the previous Examples, and further includes at least one electrode, wherein the care protocol module implements a heart monitoring protocol and the resource module includes an ECG beat detection resource module.

Example 5 includes the subject matter of any of the previous Examples, further including at least one electrode, wherein the care protocol module implements a heart monitoring protocol, the resource module includes an ECG beat detection resource module.

Example 6 includes the subject matter of Example 5, wherein the resource module is executable by the at least one processor to respond to the request at least in part by translating the level of service into an allocation requirement for a capacity of the service component, and managing the service component includes allocating the capacity of the service component to the request according to the allocation requirement, and the allocation requirement includes receiving ECG data sampled at 250 Hz or greater.

Example 7 includes the subject matter of any of the previous Examples, and further includes at least one electrode, wherein the care protocol module implements a cardiopulmonary resuscitation protocol and the resource module includes a compression resource module.

Example 8 includes the subject matter of any of the previous Examples, wherein the resource component is executable by the at least one processor to: receive a request to register a component, the request including an identifier of the component and an identifier of a type of notification for which registration is requested; store, in response to receiving the request to register, the identifier of the component and the identifier of the type; and transmit a notification of the type to the component in response to detection of a trigger of the type of the notification.

Example 9 includes the subject matter of any of the previous Examples, wherein the service component includes at least one of an electrode, an accelerometer, and a pulse oximeter.

Example 10 includes the subject matter of any of the previous Examples, wherein the service component includes at least one sensor for detecting the patient data.

Example 11 includes the subject matter of any of the previous Examples, further including an update component executable by the at least one processor to update the resource module independently from the care protocol module.

Example 12 includes a medical device comprising: a service component for use in detecting patient data; at least one processor; a first care protocol module executable by the at least one processor to provide healthcare to a patient at least in part by generating a first request for processing by the service component; and a first resource module executable by the at least one processor to identify a priority associated with the first care protocol module and to respond to the first request by processing the first request at the priority.

Example 13 includes the subject matter of Example 12, further including at least one electrode, wherein the first care protocol module implements a heart monitoring protocol and the first resource module includes an ECG beat detection resource module.

Example 14 includes the subject matter of Example 12 or 13, further including at least one electrode, wherein the first care protocol module implements a cardiopulmonary resuscitation protocol and the first resource module includes a compression resource module.

Example 15 includes the subject matter of any of Examples 12 through 14, further including a second care protocol module executable by the at least one processor to provide additional healthcare to the patient at least in part by generating a second request for processing by the service component, wherein the first resource module is executable by the at least one processor to identify a higher priority request and a lower priority request from the first request and the second request and to at least temporarily deny processing of the lower priority request in favor of processing of the higher priority request.

Example 16 includes the subject matter of Example 15, further including a defibrillation subsystem, wherein the first care protocol module implements a manual charging protocol, the second care protocol module implements a silent charging protocol, and the first resource module includes a defibrillation control resource module.

Example 17 includes the subject matter of any of Examples 12 through 16, further including a second care protocol module executable by the at least one processor to provide additional healthcare to the patient at least in part by generating a second request for processing by the service component, wherein the first resource module is executable by the at least one processor to identify a higher priority request of the first request and the second request by identifying a higher priority between the priority associated with the first care protocol module and a priority associated with the second care protocol module and identifying as the higher priority request a request associated with a care protocol module associated with the higher priority.

Example 18 includes the subject matter of any of Examples 12 through 17, further including a second care protocol module executable by the at least one processor to provide additional healthcare to the patient at least in part by generating a second request for processing by the service component, wherein the first resource module is executable by the at least one processor to identify a higher priority request and a lower priority request from the first request and the second request and to process the higher priority request prior to the lower priority request.

Example 19 includes the subject matter of Example 18, further including at least one electrode and a defibrillation subsystem, wherein the first care protocol module implements a CPR protocol, the second care protocol module implements a silent charging protocol, and the first resource module includes an ECG rhythm analysis resource module.

Example 20 is a method for offloading modular functions from a medical device to a companion computing system, the method comprising: determining if a communication network is available; in response to determining that a communication network is available, discovering one or more potential companion computing systems on the network, and executing an authentication process; and in response to determining that a given companion computing system is authentic, offloading one or more modular functions of the medical device to that companion computing system.

Example 21 includes the subject matter of Example 20 further including at least one of: in response to determining that a communication network is not available, continuing stand-alone operation of the medical device, with no offloading of modular functions; and in response to determining no companion computing systems are authentic, continuing stand-alone operation of the medical device, with no offloading of modular functions.

Example 22 includes the subject matter of Example 20 or 21, wherein the one or more modular functions of the medical device to be offloaded to the companion computing are pre-established for offloading, the method further comprising: identifying one or more modular functions approved for offloading; wherein the offloading only offloads identified approved modular functions.

Example 23 includes the subject matter of any of Examples 20 through 22 further including: determining whether offload was successful; and in response to determining that the offload was not successful, continuing stand-alone operation of the medical device, with no offloading of modular functions.

Example 24 includes the subject matter of any of Examples 20 through 23, wherein a communication link is established between the medical device and the companion computing system, the method further comprising: monitoring the communication link; and in response to determining that the communication link has failed, transitioning to stand-alone operation of the medical device, with no offloading of modular functions.

Example 25 includes the subject matter of any of Examples 20 through 24, wherein the one or more offloaded modules are pre-installed into a memory of the companion system by virtue of those modules being part of a companion application executable on the companion system, and the offloaded modules can begin execution once offloading has been signaled.

Example 26 includes the subject matter of any of Examples 20 through 25, wherein determining that a given companion computing system is authentic includes determining a companion application is installed on the companion computing system.

Example 27 includes the subject matter of any of Examples 20 through 26, wherein the one or more offloaded modules are forwarded from the medical device to the companion system via the network, and the offloaded modules can begin execution once offloading has been signaled.

Example 28 includes the subject matter of any of Examples 20 through 27, wherein the companion computing system is local to the medical device, and in addition to executing the one or more modular functions, the companion computing system provides at least one of the following support functions to the medical device: display function, video function, and audio function.

Example 29 includes the subject matter of any of Examples 20 through 27, wherein the companion computing system is remote to the medical device and part of a cloud-based service.

Example 30 includes the subject matter of any of Examples 20 through 28, wherein the companion computing system is local to the medical device, and scene data captured by the local companion computing system is provided to a remote cloud-based service, the scene data indicative of treatment being given to a patient and including at least one of audio and video captured by local companion computing system. For instance, in some cases, the scene data may be a video of the patient receiving CPR by a local caregiver, and personnel at the remote cloud-based service can evaluate the CPR technique being used and coach or otherwise instruct the caregiver to make changes, such as when to compress and when to change to mouth-to-mouth, etc. Alternatively, the remote cloud-based service may include a machine learning based process that can evaluate the video for proper technique, and give such instructive commentary through computer-generated voice.

Example 31 is a computer program product including one or more non-transitory machine readable mediums encoded with instructions that when executed by one or more processors cause a process to be carried out for offloading modular functions from a medical device to a companion computing system, the process comprising: determining if a communication network is available; in response to determining that a communication network is available, discovering one or more potential companion computing systems on the network, and executing an authentication process; and in response to determining that a given companion computing system is authentic, offloading one or more modular functions of the medical device to that companion computing system. In some embodiments, the computer program product is part of the medical device, and the one or more processors are included in the medical device. In other embodiments, the computer program product is distributed between the medical device and the companion computing system, and the one or more processors are included in the medical device and the companion computing system. A related Example is a medical system that includes the computer program product and the one or more processors. In some such cases, at least one of the medical device and the companion computing system are part of the medical system. As will be appreciated in light of this disclosure, components of the medical system may be distributed, so as to be located at different physical locations on a communication network. The physical locations may be local to one another and accessible by a common local area network, or remote from each other and accessible by a wide area network or a combination of a local area network and a wide area network.

Example 32 includes the subject matter of Example 31, the process further including at least one of: in response to determining that a communication network is not available, continuing stand-alone operation of the medical device, with no offloading of modular functions; and in response to determining no companion computing systems are authentic, continuing stand-alone operation of the medical device, with no offloading of modular functions.

Example 33 includes the subject matter of Example 31 or 32, wherein the one or more modular functions of the medical device to be offloaded to the companion computing are pre-established for offloading, the process further comprising: identifying one or more modular functions approved for offloading; wherein the offloading only offloads identified approved modular functions.

Example 34 includes the subject matter of any of Examples 31 through 33, the process further including: determining whether offload was successful; and in response to determining that the offload was not successful, continuing stand-alone operation of the medical device, with no offloading of modular functions.

Example 35 includes the subject matter of any of Examples 31 through 34, wherein a communication link is established between the medical device and the companion computing system, the process further comprising: monitoring the communication link; and in response to determining that the communication link has failed, transitioning to stand-alone operation of the medical device, with no offloading of modular functions.

Example 36 includes the subject matter of any of Examples 31 through 35, wherein the one or more offloaded modules are pre-installed into a memory of the companion system by virtue of those modules being part of a companion application executable on the companion system, and the offloaded modules can begin execution once offloading has been signaled.

Example 37 includes the subject matter of any of Examples 31 through 36, wherein determining that a given companion computing system is authentic includes determining a companion application is installed on the companion computing system.

Example 38 includes the subject matter of any of Examples 31 through 37, wherein the one or more offloaded modules are forwarded from the medical device to the companion system via the network, and the offloaded modules can begin execution once offloading has been signaled.

Example 39 includes the subject matter of any of Examples 31 through 38, wherein the companion computing system is local to the medical device, and in addition to executing the one or more modular functions, the companion computing system provides at least one of the following support functions to the medical device: display function, video function, and audio function.

Example 40 includes the subject matter of any of Examples 31 through 38, wherein the companion computing system is remote to the medical device and part of a cloud-based service.

Example 41 includes the subject matter of any of Examples 31 through 39, wherein the companion computing system is local to the medical device, and scene data captured by the local companion computing system is provided to a remote cloud-based service, the scene data indicative of treatment being given to a patient and including at least one of audio and video captured by local companion computing system.

Example 42 is a medical system comprising: one or more memories encoded with instructions; and one or more processors for executing the instructions to: determine if a communication network is available; in response to determining that a communication network is available, discover one or more potential companion computing systems on the network, and execute an authentication process; and in response to determining that a given companion computing system is authentic, offload one or more modular functions of a medical device to that companion computing system. In some embodiments, the medical system is part of the medical device, and the one or more processors are included in the medical device. In other embodiments, the medical system is distributed between the medical device and the companion computing system, and the one or more processors are included in the medical device and the companion computing system. The medical system may be, for instance, an AED or other portable medical device. In some such embodiments, the medical system further includes the companion computing system.

Example 43 includes the subject matter of Example 42, the one or more processors further to at least one of: in response to determining that a communication network is not available, continue stand-alone operation of the medical device, with no offloading of modular functions; and in response to determining no companion computing systems are authentic, continue stand-alone operation of the medical device, with no offloading of modular functions.

Example 44 includes the subject matter of Example 42 or 43, wherein the one or more modular functions of the medical device to be offloaded to the companion computing are pre-established for offloading, the one or more processors further to: identify one or more modular functions approved for offloading; wherein the offloading only offloads identified approved modular functions.

Example 45 includes the subject matter of any of Examples 42 through 44, the one or more processors further to: determine whether offload was successful; and in response to determining that the offload was not successful, continue stand-alone operation of the medical device, with no offloading of modular functions.

Example 46 includes the subject matter of any of Examples 42 through 45, wherein a communication link is established between the medical device and the companion computing system, the one or more processors to further: monitor the communication link; and in response to determining that the communication link has failed, transitioning to stand-alone operation of the medical device, with no offloading of modular functions.

Example 47 includes the subject matter of any of Examples 42 through 46, wherein the one or more offloaded modules are pre-installed into a memory of the companion system by virtue of those modules being part of a companion application executable on the companion system, and the offloaded modules can begin execution once offloading has been signaled.

Example 48 includes the subject matter of any of Examples 42 through 47, wherein determining that a given companion computing system is authentic includes determining a companion application is installed on the companion computing system.

Example 49 includes the subject matter of any of Examples 42 through 48, wherein the one or more offloaded modules are forwarded from the medical device to the companion system via the network, and the offloaded modules can begin execution once offloading has been signaled.

Example 50 includes the subject matter of any of Examples 42 through 49, wherein the companion computing system is local to the medical device, and in addition to executing the one or more modular functions, the companion computing system provides at least one of the following support functions to the medical device: display function, video function, and audio function.

Example 51 includes the subject matter of any of Examples 42 through 49, wherein the companion computing system is remote to the medical device and part of a cloud-based service.

Example 52 includes the subject matter of any of Examples 42 through 50, wherein the companion computing system is local to the medical device, and scene data captured by the local companion computing system is provided to a remote cloud-based service, the scene data indicative of treatment being given to a patient and including at least one of audio and video captured by local companion computing system.

The examples of the methods and apparatuses (including any devices, systems, etc) discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Having thus described several aspects of at least one embodiment of this disclosure, it is to be appreciated various alterations, modifications, and improvements will readily occur to those skilled in the art. Such alterations, modifications, and improvements are intended to be part of and within the scope of this disclosure. Accordingly, the foregoing description and drawings are by way of example only.

The invention claimed is:

1. A medical device comprising:
   a service component configured to detect patient data;
   at least one processor coupled to the service component;
   a first care protocol module executable by the at least one processor to provide healthcare to a patient at least in part by generating a first request for processing by the service component; and
   a resource module executable by the at least one processor to manage access to the service component by
      identifying a level of service associated with the first care protocol module, and
      responding to the first request by managing the service component to meet the level of service,
   wherein
      the first care protocol module implements a patient care protocol that includes a sequence of actions directed to the patient;
      the level of service indicates a level of performance that the first care protocol requires of the service component; and
      the resource module includes an electrocardiogram rhythm analysis resource module and is executable by the at least one processor to respond to requests from at least the first care protocol module that fall within a predetermined time window with a single calculated instance of cardiac rhythm data.

2. The medical device of claim 1, further comprising:
   a second care protocol module executable by the at least one processor to provide additional healthcare to the patient at least in part by generating a second request for processing by the service component; and
   a conflict arbitration engine executable by the at least one processor to resolve conflicts between multiple requests for processing by the service component at least in part by
      comparing the multiple requests,
      identifying a source component associated with at least one request of the multiple requests, and
      initiating processing of the at least one request.

3. The medical device of claim 1, wherein the resource module is executable by the at least one processor to respond to the first request at least in part by
   translating the level of service into an allocation requirement for a capacity of the service component, and
   managing the service component includes allocating the capacity of the service component to the first request according to the allocation requirement.

4. The medical device of claim 3, wherein
   the service component comprises at least one electrode,
   the first care protocol module implements a heart monitoring protocol,
   the resource module includes an electrocardiogram (ECG) beat detection resource module, and
   the allocation requirement includes receiving ECG data sampled at a frequency of 250 Hz or greater.

5. The medical device of claim 3, wherein
   the service component comprises at least one electrode,
   the first care protocol module implements a cardiopulmonary resuscitation protocol, and
   the resource module includes a compression resource module.

6. The medical device of claim 3, further comprising a second care protocol module executable by the at least one processor to provide additional healthcare to the patient at least in part by generating a second request for processing by the service component, wherein
   the first care protocol module implements a heart monitoring protocol, and
   the second care protocol module implements a cardiopulmonary resuscitation protocol.

7. The medical device of claim 3, further comprising a second care protocol module executable by the at least one processor to provide additional healthcare to the patient at least in part by generating a second request for processing by the service component, wherein the resource module is executable by the at least one processor to
- identify a higher priority request and a lower priority request from the first request and the second request, and
- at least temporarily deny processing of the lower priority request in favor of processing of the higher priority request.

8. The medical device of claim 7, wherein
the service component comprises a defibrillation subsystem,
the first care protocol module implements a manual charging protocol,
the second care protocol module implements a silent charging protocol, and
the resource module includes a defibrillation control resource module.

9. The medical device of claim 8, wherein the resource module is executable by the at least one processor to identify the second request as the lower priority request where the second request is received after the first request.

10. The medical device of claim 3, further comprising:
a second care protocol module executable by the at least one processor to provide additional healthcare to the patient at least in part by generating a second request for processing by the service component; and
a conflict arbitration engine executable by the at least one processor to resolve conflicts between multiple requests for processing by the service component at least in part by
receiving an arbitration request indicating the multiple requests,
comparing the multiple requests,
identifying a lower priority request of the multiple requests as being from a source component associated with a lower priority, and
transmit a notification indicating the lower priority request.

11. The medical device of claim 10, wherein
the service component comprises a defibrillation subsystem,
the first care protocol module is associated with a higher priority and implements an audible charging protocol,
the second care protocol module is associated with the lower priority and implements a silent charging protocol, and
the resource module includes a defibrillation control resource module.

12. The medical device of claim 11, wherein the defibrillation control resource module is executable by the at least one processor to:
receive, from the second care protocol module, a first charge request to charge the defibrillator subsystem;
receive, from the first care protocol module after the first charge request, a second charge request to charge the defibrillator subsystem;
transmit an arbitration request to the conflict arbitration engine, the arbitration request indicating the first charge request and the second charge request;
receive a notification from the conflict arbitration engine indicating that the first charge request is the lower priority request; and
transmit a notification to the second care protocol module indicating that the first charge requested is canceled.

13. The medical device of claim 3, further comprising a second care protocol module executable by the at least one processor to provide additional healthcare to the patient at least in part by generating a second request for processing by the service component, wherein the resource module is executable by the at least one processor to:
identify a higher priority request and a lower priority request from the first request and the second request, and
process the higher priority request prior to the lower priority request.

14. The medical device of claim 3, further comprising a second care protocol module executable by the at least one processor to provide additional healthcare to the patient at least in part by generating a second request for processing by the service component, wherein the resource module is executable by the at least one processor to identify a higher priority request of the first request and the second request by:
identifying a higher priority between a priority associated with the first care protocol module and a priority associated with the second care protocol module, and
identifying as the higher priority request a request associated with a care protocol module associated with the higher priority.

15. The medical device of claim 1, wherein the resource module is executable by the at least one processor to:
receive a registration request to register the service component, the registration request including
a first identifier of the service component, and
a second identifier of a type of notification for which registration is requested;
store, in response to receiving the registration request, the first identifier and the second identifier; and
transmit a response to the service component to indicate successful registration of the service component.

16. The medical device of claim 1, wherein the service component includes at least one of an electrode, an accelerometer, and a pulse oximeter.

17. The medical device of claim 1, wherein the service component includes at least one sensor for detecting the patient data.

18. The medical device of claim 1, further comprising an update component executable by the at least one processor to update the resource module independently from the first care protocol module.

19. The medical device of claim 1, wherein the predetermined time window is less than 0.8 seconds.

* * * * *